United States Patent
Dyckman et al.

(10) Patent No.: US 7,390,810 B2
(45) Date of Patent: Jun. 24, 2008

(54) PYRAZOLE-AMINE COMPOUNDS USEFUL AS KINASE INHIBITORS

(75) Inventors: Alaric J. Dyckman, Lawrenceville, NJ (US); Jagabandhu Das, Mercerville, NJ (US); Katerina Leftheris, Skillman, NJ (US); Chunjian Liu, Pennington, NJ (US); Robert V. Moquin, East Brunswick, NJ (US); Stephen T. Wrobleski, Whitehouse Station, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/931,309

(22) Filed: Oct. 31, 2007

(65) Prior Publication Data

US 2008/0108626 A1 May 8, 2008

Related U.S. Application Data

(62) Division of application No. 10/837,778, filed on May 3, 2004.

(60) Provisional application No. 60/467,029, filed on May 1, 2003.

(51) Int. Cl.
*A61K 31/501* (2006.01)
*C07F 9/02* (2006.01)
*C07D 401/12* (2006.01)
*C07D 271/06* (2006.01)
*C07D 277/84* (2006.01)

(52) U.S. Cl. .......... 514/252.01; 514/277; 514/311; 514/364; 514/406; 544/232; 546/256; 546/138; 548/131; 548/152; 548/247; 548/364.1

(58) Field of Classification Search ......... 514/252.01, 514/277, 311, 364; 544/232; 546/256, 138; 548/131, 152, 247, 364.1
See application file for complete search history.

(56) References Cited

U.S. PATENT DOCUMENTS

| | | | |
|---|---|---|---|
| 6,147,080 | A | 11/2000 | Bemis et al. |
| 6,821,965 | B1 | 11/2004 | Brown et al. |
| 2002/0065270 | A1 | 5/2002 | Moriarty et al. |
| 2002/0137747 | A1 | 9/2002 | Moriarty et al. |
| 2003/0139435 | A1 | 7/2003 | Ahmed et al. |
| 2005/0004176 | A1* | 1/2005 | Dyckman et al. ........... 514/341 |
| 2005/0176965 | A1 | 8/2005 | Chen et al. |
| 2006/0004067 | A1 | 1/2006 | Chen et al. |
| 2006/0069132 | A1 | 3/2006 | Armel et al. |

FOREIGN PATENT DOCUMENTS

| | | |
|---|---|---|
| EP | 1 102 743 B1 | 7/2002 |
| WO | WO 01/46172 | 6/2001 |
| WO | WO 02/062804 | 8/2002 |
| WO | WO2004/035545 A2 | 4/2004 |
| WO | WO2004/071440 A2 | 8/2004 |
| WO | WO2004/098518 A2 | 11/2004 |
| WO | WO2004/099156 A1 | 11/2004 |
| WO | WO2004/106324 A1 | 12/2004 |
| WO | WO2005/042537 A1 | 5/2005 |
| WO | WO2005/061465 A1 | 7/2005 |
| WO | WO2005/077945 A2 | 8/2005 |
| WO | WO2007/002742 A1 | 1/2007 |

OTHER PUBLICATIONS

Cheng, C.C. et al., "Potential Purine Antagonists. VI. Synthesis of 1-Aklyl- and 1-Aryl-4-substituted Pyrazolo[3,4-*d*]pyrimidines", J. Org. Chem., vol. 21, pp. 1240-1256 (1956).

Deshayes, C. et al., "Synthesis of some Substituted 3-Alkenyl-1-phenylpyrazoles", J. Heterocyclic Chem., vol. 16, pp. 657-660 (1979).

Greene, T.W. et al., Protective Groups in Organic Synthesis, Third Edition, John Wiley & Sons, Inc., publ., pp. xi-xii (table of contents) (1999).

Henry, J.R. et al., "p38 mitogen-activated protein kinase as a target for drug discovery", Drugs of the Future, vol. 24, No. 12, pp. 1345-1354 (1999).

Iwata, S. et al., "Synthesis of (Trifluoromethyl)pyrazoles via 1,3-Dipolar Cycloaddition Reaction and Their Derivation to Photochromic Fulgides", Nippon Kagaku Kaishi, vol. 10, pp. 1144-1147 (1992) (with English abstract).

Joule, J.A. et al., Chapter 22: "1,2-Azoles: pyrazoles, isothiazoles and isoxazoles: reactions and synthesis", Heterocyclic Chemistry, Third Edition, Stanley Thornes (Publishers) Ltd., publ., pp. 394-408 (1995).

(Continued)

*Primary Examiner*—James O. Wilson
*Assistant Examiner*—Ebenezer Sackey
(74) *Attorney, Agent, or Firm*—Rosemary M. Miano; Burton Rodney; Anastasia P. Winslow

(57) ABSTRACT

The present invention provides pyrazole derived compounds of formula (I)

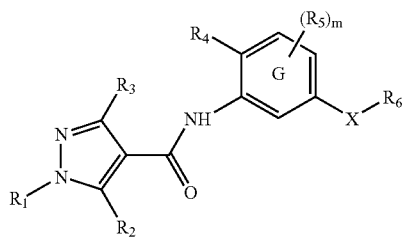

useful for treating p38 kinase-associated conditions, where G, X, $R_1$, $R_2$, $R_3$, $R_4$, $R_5$, $R_6$ and m are as defined herein. The invention further pertains to pharmaceutical compositions containing at least one compound according to the invention useful for treating p38 kinase-associated conditions, and methods of inhibiting the activity of p38 kinase in a mammal.

17 Claims, No Drawings

OTHER PUBLICATIONS

Manferdini, M. et al., "Chemoselective Synthesis of Pyrazole Derivatives via β-Enamino Keto Esters", Heterocycles, vol. 53, No. 12, pp. 2775-2780 (2000).

Manning, G. et al., "The Protein Kinase Complement of the Human Genome", Science, vol. 298, pp. 1912-1916, 1933-1934 (2002).

Moreland, L.W. et al., "Etanercept Therapy in Rheumatoid Arthritis: A Randomized, Controlled Trail", Ann. Intern. Med., vol. 130, No. 6, pp. 478-486 (1999).

Rankin, E.C.C. et al., "The Therapeutic Effects of an Engineered Human Anti-Tumour Necrosis Factor Alpha Antibody (CDP571) in Rheumatoid Arthritis", British Journal of Rheumatology, vol. 34, No. 4, pp. 334-342 (1995).

Salituro, F.G. et al., "Inhibitors of p38 MAP Kinase: Therapeutic Intervention in Cytokine-Mediated Diseases", Current Medicinal Chemistry, vol. 6, No. 9, pp. 807-823 (1999).

Schlosser, M. et al., "Switchable Reactivity: The Site-Selective Functionalization of Trifluoromethyl-Substituted Pyrazoles", Eur. J. Org. Chem., vol. 17, pp. 2913-2920 (2002).

Vicentini, C.B. et al., "A New Synthetic Entry to 3-Carboxamido-4-carboxylic Acid Derivatives of Isoxazole and Pyrazole", J. Heterocyclic Chem., vol. 37, pp. 175-180 (2000).

\* cited by examiner

US 7,390,810 B2

PYRAZOLE-AMINE COMPOUNDS USEFUL AS KINASE INHIBITORS

RELATED APPLICATION

This application is a divisional of U.S. application Ser. No. 10/837,778, filed May 3, 2004, which claims the benefit of U.S. Provisional Application Ser. No. 60/467,029, filed May 1, 2003. Each of the priority applications are incorporated by reference in their entireties.

FIELD OF THE INVENTION

This invention relates to pyrazole derived compounds useful for treating p38 kinase-associated conditions. The invention further pertains to pharmaceutical compositions containing at least one compound according to the invention useful for treating p38 kinase-associated conditions, and methods of inhibiting the activity of p38 kinase in a mammal.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., *Drugs Fut.*, Vol. 24 (1999), at pp. 1345-54; Salituro et al., *Curr. Med. Chem.*, Vol. 6 (1999), at pp. 807-823]. Evidence in human patients indicates that protein antagonists of cytokines are effective in treating chronic inflammatory diseases, such as, for example, monoclonal antibody to TNF-α (Enbrel) [Rankin et al., *Br. J. Rheumatol.*, Vol. 34 (1995), at pp. 334-42], and soluble TNF-α receptor-Fc fusion protein (Etanercept) [Moreland et al., *Ann. Intern. Med.*, Vol. 130 (1999), at pp. 478-86].

The biosynthesis of TNF-α occurs in many cell types in response to an external stimulus, such as, for example, a mitogen, an infectious organism, or trauma. Important mediators of TNF-α production include the mitogen-activated protein (MAP) kinases, a family of Ser/Thr protein kinases that activate their substrates by phosphorylation. The MAP kinases are activated in response to various stress stimuli, including but not limited to proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38-α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has established the effectiveness of p38 inhibitors in treating those diseases. The present invention provides pyrazole derived compounds, useful as kinase inhibitors, in particular, as inhibitors of p38 kinase.

DESCRIPTION OF THE INVENTION

The present invention pertains to methods of treating p-38 associated conditions, by administering compounds having the formula (I), and/or pharmaceutically acceptable salts of solvates thereof.

Additionally, according to another aspect of the invention, there are provided pyrazole derived compounds of formula (I)

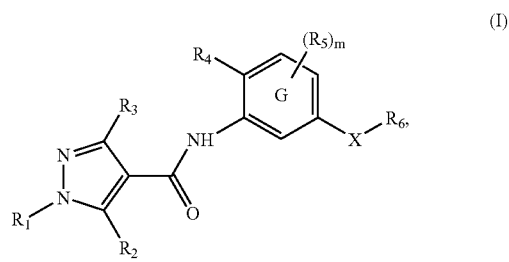

useful for treating p38 kinase-associated conditions, where G, X, $R_1$, $R_2$, $R_3$, $R_4$, $R_5$, $R_6$ and m are as defined herein.

According to one aspect of the invention, there is provided pyrazole derived compounds of formula (I),

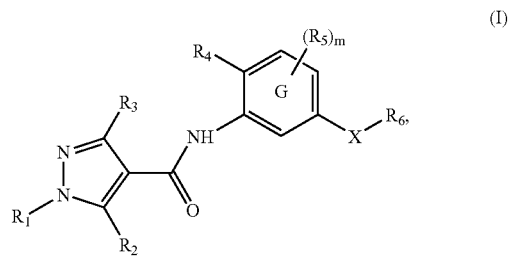

wherein G is phenyl or pyridyl;

$R_1$ is hydrogen, alkyl, substituted alkyl, aryl, substituted aryl, heteroaryl, substituted heteroaryl, cycloalkyl, substituted cycloalkyl, heterocyclo or substituted heterocyclo, or $C(\!\!=\!\!O)R_{18}$;

$R_2$ is hydrogen, hydroxyl(alkyl), alkoxy(alkyl), haloalkyl, halogen, cyanoalkyl, alkoxy, substituted alkoxy, or $R_{2a}$, wherein $R_{2a}$ is $C_{1-6}$alkyl, amino, alkylamino, substituted alkylamino, cycloamino, substituted cycloamino, or $C_{1-6}$alkyl substituted with one to two of amino, alkylamino, substituted alkylamino, cycloamino, and/or substituted cycloamino;

$R_3$ is hydrogen, haloalkyl, haloalkoxy, halogen, cyano, nitro, $C_{1-4}$alkyl, substituted $C_{1-4}$alkyl, $NR_{11}R_{12}$, or $OR_{11}$;

$R_4$ is hydrogen, $C_{1-4}$alkyl, substituted $C_{1-4}$alkyl, halogen, haloalkyl, haloalkoxy, cyano, nitro, or $OR_{13}$;

$R_5$ is at each occurrence independently selected from haloalkyl, haloalkoxy, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, heteroaryl or substituted heteroaryl, $OR_{13}$, $SR_{13}$, $S(\!\!=\!\!O)R_{14}$, $S(\!\!=\!\!O)_2R_{14}$, $P(\!\!=\!\!O)_2R_{14}$, $S(\!\!=\!\!O)_2OR_{15}$, $P(\!\!=\!\!O)_2OR_{14}$, $NR_{13}R_{14}$, $NR_{13}S(\!\!=\!\!O)_2R_{15}$, $NR_{13}P(\!\!=\!\!O)_2R_{14}$, $S(\!\!=\!\!O)_2NR_{13}R_{14}$, $P(\!\!=\!\!O)_2NR_{13}R_{14}$, $C(\!\!=\!\!O)OR_{13}$, $C(\!\!=\!\!O)R_{13}$, $C(\!\!=\!\!O)NR_{13}R_{14}$, $OC(\!\!=\!\!O)R_{13}$, $OC(\!\!=\!\!O)NR_{13}R_{14}$, $NR_{13}C(\!\!=\!\!O)OR_{14}$, $NR_{16}C$ (=O)NR$_{13}$R$_{14}$, NR$_{16}$S(=O)$_2$NR$_{13}$R$_{14}$, NR$_{16}$P(=O)$_2$NR$_{13}$R$_{14}$, NR$_{13}$C(=O)R$_{14}$, and/or NR$_{13}$P(=O)$_2$R$_{14}$;

X is —(C=O)NH—, —NH(C=O)—, —NH(C=O)—, —SO$_2$NH—, —CO$_2$—, or is absent;

R$_6$ is hydrogen, alkyl or substituted alkyl, alkoxy or substituted alkoxy, phenoxy or substituted phenoxy, cycloalkyl or substituted cycloalkyl, heterocycle or substituted heterocycle, aryl or substituted aryl, heteroaryl or substituted heteroaryl; or where X is absent, R$_6$ can also be selected from halogen, cyano, trifluoromethyl, alkyl, amino, and/or alkylamino; or alternatively, R$_6$ is joined together with a group R$_5$ on an adjacent carbon atom to form an optionally-substituted, fused five to six membered heterocyclic or carbocyclic ring;

R$_{11}$, R$_{12}$, R$_{13}$, R$_{14}$, R$_{15}$, R$_{16}$ and R$_{17}$ are independently at each occurrence selected from hydrogen, alkyl, substituted alkyl, cycloalkyl or substituted cycloalkyl, heterocycle or substituted heterocycle, aryl or substituted aryl, and heteroaryl or substituted heteroaryl, except R$_{15}$ is not hydrogen;

R$_{18}$ is hydrogen, alkyl or substituted alkyl, alkenyl or substituted alkenyl, alkynyl or substituted alkynyl, cycloalkyl or substituted cycloalkyl, heterocycle or substituted heterocycle, heteroaryl, or substituted heteroaryl, aryl or substituted aryl; and m is 0, 1, 2 or 3;

provided that the following compounds are excluded:

(A) compounds having the formula (I), wherein R$_1$ is an optionally-substituted phenyl, pyridyl, pyridazinyl, pyrimidinyl, or pyrazinyl ring; R$_2$ is R$_{2a}$; R$_3$ is hydrogen; R$_4$ is methyl; m is 0; and X—R$_6$ is —C(=O)NH(C$_{1-6}$alkyl), —C(=O)NH(cyclopropyl), or optionally-substituted oxadiazolyl;

(B) compounds having formula (Ix):

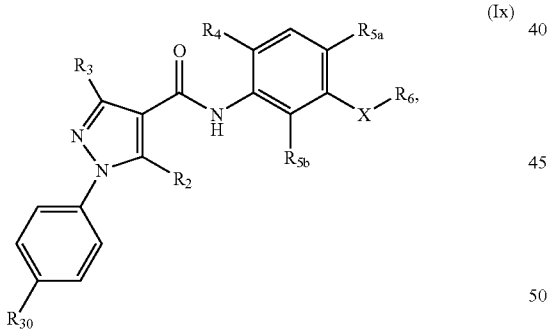

(i) simultaneously, R$_{30}$ is trifluoromethyl, R$_2$ is methyl, R$_3$ is hydrogen, R$_4$ is bromo, X—R$_6$ is hydrogen, R$_{5b}$ is hydrogen, and R$_{5a}$ is methyl or

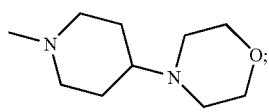

(ii) simultaneously, R$_{30}$ is hydrogen or methoxy, R$_2$ is hydrogen or methyl, R$_3$ is hydrogen, R$_4$ is hydrogen, X—R$_6$ is hydrogen, R$_{5b}$ is hydrogen, and R$_{5a}$ is trifluoromethyl;

(iii) simultaneously, R$_{30}$ is chloro, R$_2$ is hydrogen, R$_3$ is hydrogen, R$_4$ is hydrogen, X—R$_6$ is cyano, R$_{5b}$ is hydrogen, and R$_{5a}$ is SR$_{17}$ wherein R$_{17}$ is morpholinylalkyl;

(iv) simultaneously, R$_{30}$ is fluoro, R$_2$ is methyl, R$_3$ is hydrogen, R$_4$ is hydrogen, X—R$_6$ is cyano, R$_{5b}$ is hydrogen, and R$_{5a}$ is N-piperidinyl;

(v) simultaneously, R$_{30}$ is halogen, R$_2$ is hydrogen or methyl, R$_3$ is hydrogen, R$_4$ is hydrogen, X—R$_6$ is cyano, R$_{5b}$ is hydrogen, and R$_{5a}$ is heterocyclo or substituted heterocyclo;

(vi) simultaneously, R$_{30}$ is chloro, R$_2$ is trifluoromethyl, R$_3$ is hydrogen, R$_4$ is hydrogen, X—R$_6$ is SO$_2$NH(cycloalkyl), and R$_{5a}$ and R$_{5b}$ are hydrogen;

(vii) simultaneously, R$_{30}$ is hydrogen, R$_2$ is trifluoromethyl, R$_3$ is hydrogen, R$_4$ is hydrogen, X—R$_6$ is hydrogen, R$_{5b}$ is hydrogen, and R$_{5a}$ is substituted alkyl;

(viii) simultaneously, R$_{30}$ is hydrogen, R$_2$ is trifluoromethyl, R$_3$ is hydrogen, R$_4$ is methyl, X—R$_6$ is hydrogen, R$_{5b}$ is —C(=ONH(alkyl), and R$_{5a}$ is hydrogen; and (ix) simultaneously, R$_{30}$ is methoxy, R$_2$ is methyl, R$_3$ is hydrogen, R$_4$ is methyl, X—R$_6$ is a bicyclicheterocyclo(alkyl) or bicyclicheteroaryl(alkyl), and R$_{5a}$ and R$_{5b}$ are hydrogen; and (C) compounds having the formula (Iy),

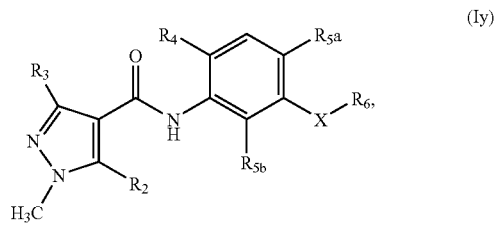

wherein (i) simultaneously, R$_2$ is hydrogen, R$_3$ is trifluoromethyl, R$_4$ is bromo, X—R$_6$ is hydrogen, R$_{5a}$ is trifluoromethyl, and R$_{5b}$ is bromo;

and wherein (ii) R$_2$ is methyl, R$_3$ is hydrogen, R$_4$ is hydrogen, X—R$_6$ is cyano, R$_{5a}$ is alkoxy, and R$_{5b}$ is hydrogen.

According to one aspect of the invention, there is provided a method of using at least one compound according to formula (I) herein, for modulating a p38 kinase in a mammal, wherein the at least one compound has the formula (I),

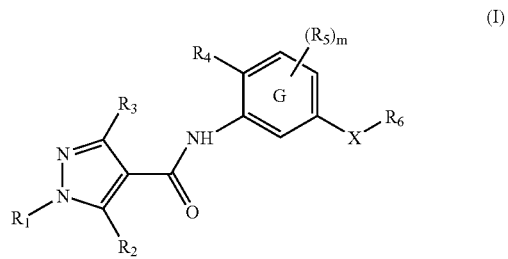

wherein G is phenyl or pyridyl;

R₁ is hydrogen, alkyl, substituted alkyl, aryl, substituted aryl, heteroaryl, substituted heteroaryl, cycloalkyl, substituted cycloalkyl, heterocyclo or substituted heterocyclo, or C(=O)R$_{18}$;

R₂ is hydrogen, hydroxyl(alkyl), alkoxy(alkyl), haloalkyl, halogen, cyanoalkyl, alkoxy, substituted alkoxy, or R$_{2a}$, wherein R$_{2a}$ is C$_{1-6}$alkyl, amino, alkylamino, substituted alkylamino, cycloamino, substituted cycloamino, or C$_{1-6}$alkyl substituted with one to two of amino, alkylamino, substituted alkylamino, cycloamino, and/or substituted cycloamino;

R₃ is hydrogen, haloalkyl, haloalkoxy, halogen, cyano, nitro, C$_{1-4}$alkyl, substituted C$_{1-4}$alkyl, NR$_{11}$R$_{12}$, or OR$_{11}$;

R₄ is hydrogen, C$_{1-4}$alkyl, substituted C$_{1-4}$alkyl, halogen, haloalkyl, haloalkoxy, cyano, nitro, or OR$_{13}$;

R₅ is at each occurrence independently selected from haloalkyl, haloalkoxy, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, heteroaryl or substituted heteroaryl, OR$_{13}$, SR$_{13}$, S(=O)R$_{14}$, S(=O)₂R$_{14}$, P(=O)₂R$_{14}$, S(=O)₂OR$_{15}$, P(=O)₂OR$_{14}$, NR$_{13}$R$_{14}$, NR$_{13}$S(=O)₂R$_{15}$, NR$_{13}$P(=O)₂R$_{14}$, S(=O)₂NR$_{13}$R$_{14}$, P(=O)₂NR$_{13}$R$_{14}$, C(=O)OR$_{13}$, C(=O)R$_{13}$, C(=O)NR$_{13}$R$_{14}$, OC(=O)R$_{13}$, OC(=O)NR$_{13}$R$_{14}$, NR$_{13}$C(=O)OR$_{14}$, NR$_{16}$C(=O)NR$_{13}$R$_{14}$, NR$_{16}$S(=O)₂NR$_{13}$R$_{14}$, NR$_{16}$P(=O)₂NR$_{13}$R$_{14}$, NR$_{13}$C(=O)R$_{14}$, and/or NR$_{13}$P(=O)₂R$_{14}$;

X is —(C=O)NH—, —NH(C=O)—, —NH(C=O)—, —SO₂NH—, —CO₂—, or is absent;

R₆ is hydrogen, alkyl or substituted alkyl, alkoxy or substituted alkoxy, phenoxy or substituted phenoxy, cycloalkyl or substituted cycloalkyl, heterocycle or substituted heterocycle, aryl or substituted aryl, heteroaryl or substituted heteroaryl; or where X is absent, R₆ can also be selected from halogen, cyano, trifluoromethyl, alkyl, amino, and/or alkylamino; or alternatively, R₆ is joined together with a group R₅ on an adjacent carbon atom to form an optionally-substituted, fused five to six membered heterocyclic or carbocyclic ring;

R$_{11}$, R$_{12}$, R$_{13}$, R$_{14}$, R$_{15}$, R$_{16}$ and R$_{17}$ are independently at each occurrence selected from hydrogen, alkyl, substituted alkyl, cycloalkyl or substituted cycloalkyl, heterocycle or substituted heterocycle, aryl or substituted aryl, and heteroaryl or substituted heteroaryl, except R$_{15}$ is not hydrogen;

R$_{18}$ is hydrogen, alkyl or substituted alkyl, alkenyl or substituted alkenyl, alkynyl or substituted alkynyl, cycloalkyl or substituted cycloalkyl, heterocycle or substituted heterocycle, heteroaryl, or substituted heteroaryl, aryl or substituted aryl; and m is 0, 1, 2 or 3;

provided that the method does not include administration of compounds wherein R₁ is an optionally-substituted phenyl, pyridyl, pyridazinyl, pyrimidinyl, or pyrazinyl ring;

R₂ is R$_{2a}$; R₃ is hydrogen, R₄ is methyl; m is 0; and X—R₆ is —C(=O)NH(C$_{1-6}$alkyl), —C(=O)NH(cyclopropyl), or optionally-substituted oxadiazolyl.

Further aspects of the invention will be apparent to one skilled in the field upon reading the disclosure herein.

DEFINITIONS

The following are definitions of terms used in the present specification and claims. The initial definition provided for a group or term herein applies to that group or term throughout the present specification and claims herein individually or as part of another group, unless otherwise indicated.

The terms "alkyl" and "alk" refer to a straight or branched chain alkane (hydrocarbon) radical containing from 1 to 12 carbon atoms, preferably 1 to 6 carbon atoms. Exemplary "alkyl" groups include methyl, ethyl, propyl, isopropyl, 1-methylpropyl, n-butyl, t-butyl, isobutyl, pentyl, hexyl, isohexyl, heptyl, dimethylpentyl, diethylpentyl, octyl, 2,2,4-trimethylpentyl, nonyl, decyl, undecyl, dodecyl, and the like. The term "C$_1$-C$_4$ alkyl" refers to a straight or branched chain alkane (hydrocarbon) radical containing from 1 to 4 carbon atoms, such as methyl, ethyl, propyl, isopropyl, n-butyl, t-butyl, and isobutyl. A lower alkyl is a "C$_1$-C$_4$ alkyl." When alkyl, lower alkyl (or C$_1$-C$_4$alkyl) is used as a suffix following another named group, such as "hydroxyalkyl" of hydroxyl (lower alkyl), this is intended to refer to an alkyl or lower alkyl (C$_1$-C$_4$alkyl) having bonded thereto one, two or three of the other, specifically-named group(s) at any point of attachment on either the straight or branched chain of the alkyl. As a further example, arylalkyl includes groups such as benzyl or phenylethyl. When the term "substituted" is used with such groups, as in "substituted arylalkyl" or "substituted alkoxyalkyl," it should be understood that either the alkyl moiety, the other named moiety, or both, may be substituted with groups selected from those recited herein as appropriate, e.g., for the alkyl moiety, groups may be selected from those recited below for substituted alkyl, and for the other, specifically-named group, groups may be selected from those recited below for that group.

"Substituted alkyl" refers to an alkyl group as defined above substituted with one or more substituents, preferably 1 to 4 substituents, more preferably 1 to 2 substituents, at any available point of attachment on the straight and/or branched chain. Exemplary substituents may include but are not limited to one or more of halogen, haloalkyl (e.g., a single halo substituent or multiple halo substituents forming, in the latter case, groups such as a perfluoroalkyl group including for example, —CHCl₂ and/or CF₃), haloalkoxyl (e.g., including trifluoromethoxy), cyano, nitro, alkenyl, alkynyl, cycloalkyl, heterocycle, heteroaryl, aryl, OR$_a$, SR$_a$, S(=O)R$_e$, S(=O)₂R$_e$, P(=O)₂R$_e$, S(=O)₂OR$_e$, P(=O)₂OR$_e$, P(=O)(OR)₂, NR$_b$R$_c$, NR$_b$S(=O)₂R$_e$, NR$_b$P(=O)₂R$_e$, S(=O)₂NR$_b$R$_c$, P(=O)₂NR$_b$R$_c$, C(=O)OR$_a$, C(=O)R$_a$, C(=O)NR$_b$R$_c$, OC(=O)R$_a$, C(=O)ONR$_b$R$_c$, OC(=O)NR$_b$R$_c$, NR$_b$C(=O)OR$_a$, NR$_d$C(=O)NR$_b$R$_c$, NR$_d$S(=O)₂NR$_b$R$_c$, NR$_d$P(=O)₂NR$_b$R$_c$, NR$_b$C(=O)R$_a$, and/or NR$_b$P(=O)₂R$_e$, wherein R$_a$, R$_b$, R$_c$, R$_d$ and R$_e$ are selected from hydrogen, alkyl, alkenyl, aminoalkyl, alkylaminoalkyl, cycloalkyl(alkyl), aryl(alkyl), heterocyclo(alkyl), heteroaryl(alkyl), cycloalkyl, aryl, heterocyclo, and/or heteroaryl, except R$_e$ is not hydrogen; and additionally, when R$_b$ and R$_c$ are attached to the same nitrogen atom, they may be joined together to form a cycloamino group. Each of R$_a$, R$_b$, R$_c$, R$_d$ and/or R$_e$ on the alkyl and/or cyclic moieties in turn may be optionally substituted with one to three groups, preferably substituted with up to two groups (0 to 2 groups), selected from lower alkyl, lower alkenyl, R$_f$, and a lower alkyl or lower alkenyl substituted with one to two R$_f$, wherein R$_f$ is selected from one or more of cyano, halogen, haloC$_1$-C$_4$alkyl, haloC$_1$-C$_4$alkoxy, keto (=O) (where valence allows), nitro, OH, O(C$_1$-C$_4$alkyl), SH, S(C$_1$-C$_4$alkyl), S(=O)(C$_1$-C$_4$alkyl), S(=O)₂(C$_1$-C$_4$alkyl), NH₂, NH(C$_1$-C$_4$alkyl), N(C$_1$-C$_4$alkyl)₂, NH(cycloalkyl), NH(phenyl), phenyl, benzyl, phenoxy, benzyloxy, NHS(=O)₂(alkyl), S(=O)₂NH₂, S(=O)₂NH(C$_1$-C$_4$alkyl), S(=O)₂N(C$_1$-C$_4$alkyl)₂, S(=O)₂NH(cycloalkyl), S(=O)₂NH(phenyl), C(=O)OH, C(=O)O(C$_1$-C$_4$alkyl), C(=O)H, C(=O)(C$_1$-C$_4$alkyl), C(=O)NH$_2$, C(=O)NH(C$_1$-C$_4$alkyl), C(=O)N(C$_1$-C$_4$alkyl)$_2$, C(=O)NH(cycloalkyl), C(=O)NH (phenyl), C(=O)NH(phenyl), C(=O)ONH$_2$, C(=O)ONH (C$_1$-C$_4$alkyl), C(=O)ON(C$_1$-C$_4$alkyl)$_2$, C(=O)ONH(cycloalkyl), C(=O)ONH(phenyl), NHC(=O)OC$_1$-C$_4$alkyl, N(C$_1$-C$_4$alkyl)C(=O)O(C$_1$-C$_4$alkyl), NHC(=O)NH$_2$, NHC (=O)NH(C$_1$-C$_4$alkyl), NHC(=O)N(C$_1$-C$_4$alkyl)$_2$, NHC (=O)NH(cycloalkyl), NHC(=O)NH(phenyl), NHC(=O) H, and/or NHC(=O)(C$_1$-C$_4$alkyl).

The term "alkenyl" refers to a straight or branched chain hydrocarbon radical containing from 2 to 12 carbon atoms and at least one carbon-carbon double bond. Exemplary such groups include ethenyl and allyl. Lower alkenyl means an alkenyl group of 2 to 4 carbon atoms. "Substituted alkenyl" refers to an alkenyl group substituted with one or more substituents, preferably 1 to 4 substituents, more preferably 1 to 2 substituents, at any available point of attachment. Exemplary substituents may include, but are not limited to, alkyl, substituted alkyl, and those groups recited above as exemplary substituents for substituted alkyl groups.

The term "alkynyl" refers to a straight or branched chain hydrocarbon radical containing from 2 to 12 carbon atoms and at least one carbon-to-carbon triple bond. Exemplary such groups include ethynyl. "Substituted alkynyl" refers to an alkynyl group substituted with one or more substituents, preferably 1 to 4 substituents, more preferably 1 to 2 substituents, at any available point of attachment. Exemplary substituents include, but are not limited to, alkyl, substituted alkyl, and those groups recited above as exemplary substituents for substituted alkyl groups.

The term "alkoxy" refers to the group OR$_g$, wherein R$_g$ is selected from alkyl, alkenyl, or cycloalkyl. A C$_1$-C$_4$alkoxy is an alkoxy group OR$_{g'}$ wherein R$_{g'}$ is a C$_1$-C$_4$alkyl or C$_3$-C$_4$cycloalkyl. A substituted alkoxy group is an alkoxy group as defined above wherein at least one of the alkyl, alkenyl, and/or cycloalkyl moieties is substituted with one or more, preferably 1 to 4, more preferably 1 to 2, groups selected from those recited above for substituted alkenyl groups.

The term "amino" refers to NH$_2$, and an alkylamino refers to an amino group wherein one or both of the hydrogen atoms is or are replaced with a group chosen from alkyl, alkenyl, and/or cycloalkyl. Thus, alkylamino refers to the group NR$_h$R$_i$, wherein R$_h$ and R$_i$ are selected from hydrogen, alkyl, alkenyl, and/or cycloalkyl, provided R$_h$ and R$_i$ are not both hydrogen. "Aminoalkyl" refers to an alkyl group as defined above substituted with an amino group, and an "alkylaminoalkyl" refers to an alkyl group as defined above substituted with one or more alkylamino groups. A substituted alkylamino group is an alkylamino group wherein at least one of the alkyl, alkenyl, and/or cycloalkyl moieties is substituted with one or more, preferably 1 to 4, more preferably 1 to 2, groups selected from those recited herein as appropriate for the recited moiety. Thus, for example, an optionally-substituted alkylamino group refers to the group —NR'R", wherein R' and R" are selected from hydrogen, alkyl, substituted alkyl, alkenyl, substituted alkenyl, cycloalkyl, and substituted cycloalkyl, provided R' and R" are not both hydrogen, as in that case the group is amino and not optionally-substituted alkylamino.

A cycloamino group refers to a group —NR'R", wherein R' and R" join to form a monocyclic heterocyclo ring, such as, for example, N-morpholinyl, N-piperidinyl, N-piperazinyl and the like. A "substituted cycloamino" is a cycloamino group having one or more, preferably one to 4, more preferably one to 2, substituents selected from those recited below for substituted heterocyclo groups.

The term "alkylthio" refers to the group SR$_g$, wherein R$_g$ is selected from alkyl, alkenyl, and cycloalkyl. A C$_1$-C$_4$alkylthio is an alkylthio group SR$_{g'}$ wherein R$_{g'}$ is a C$_1$-C$_4$alkyl or C$_3$-C$_4$cycloalkyl. A substituted alkylthio group is an alkylthio group wherein at least one of the alkyl, alkenyl, and/or cycloalkyl moieties is substituted with one or more, preferably 1 to 4, more preferably 1 to 2, groups selected from those recited above for substituted alkenyl groups.

The term "aryl" refers to cyclic aromatic hydrocarbon groups which have 1 to 3 aromatic rings, including phenyl and naphthyl. The aryl group may have fused thereto a second or third ring which is a heterocyclo, cycloalkyl, or heteroaryl ring, provided in that case the point of attachment will be to the aryl portion of the ring system. Thus, exemplary aryl groups include,

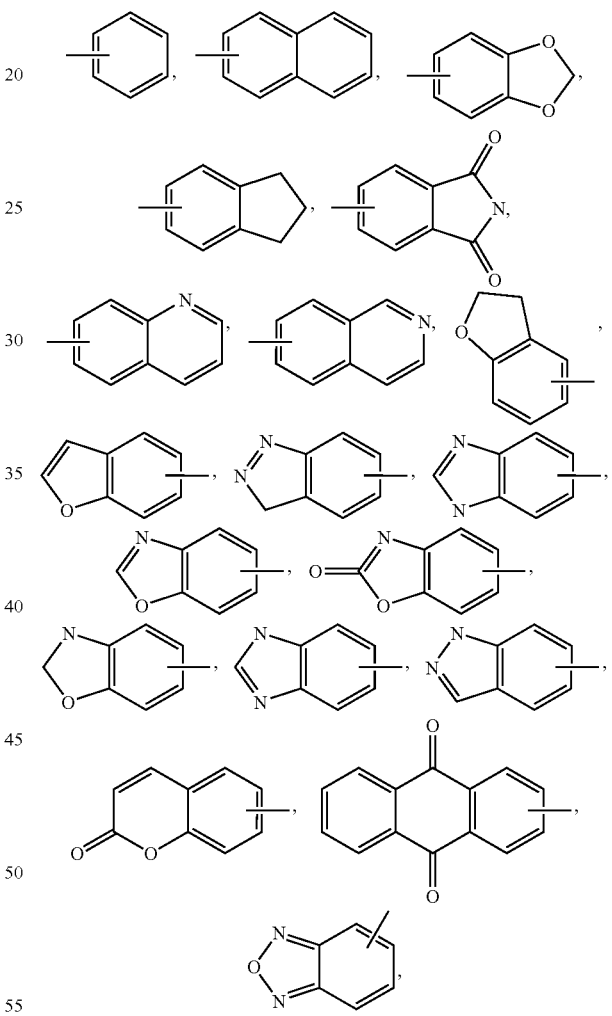

and so forth.

"Substituted aryl" refers to an aryl group substituted by one or more substituents, preferably 1 to 3 substituents, more preferably 1 to 2 substituents, at any point of attachment of the aryl ring and/or of any further ring fused thereto. Exemplary substituents include, but are not limited to, alkyl, substituted alkyl, and where valence allows those groups recited above as exemplary substituents for substituted alkyl groups.

The term "cycloalkyl" refers to a fully saturated and partially unsaturated cyclic hydrocarbon group containing from 1 to 3 rings and 3 to 8 carbons per ring. Exemplary such groups include cyclopropyl, cyclobutyl, cyclopentyl, cyclohexyl, cycloheptyl, cyclobutenyl, cyclopentenyl, cyclohexenyl, etc. A cycloalkyl ring may have a carbon ring atom replaced with a carbonyl group (C=O), as illustrated below. Cycloalkyl groups include such rings having a second or third ring fused thereto that is a heterocyclo, heteroaryl, or aryl group, provided that in such cases the point of attachment is to the cycloalkyl portion of the ring system. The term "cycloalkyl" also includes such rings having a second or third ring attached to the ring or ring system in a spiro fashion wherein the spiro ring is either a heterocyclo or carbocyclic ring. "Substituted cycloalkyl" refers to a cycloalkyl group as defined above having one or more substituents, preferably 1 to 4 substituents, more preferably 1 to 2 substituents, at any available point of attachment on either the cycloalkyl ring and where valence allows on any rings fused or attached thereto. Exemplary substituents include, but are not limited to, alkyl, substituted alkyl, and those groups recited above as exemplary substituents for substituted alkyl groups.

Thus, as an illustration non-limiting examples of cycloalkyl rings may include,

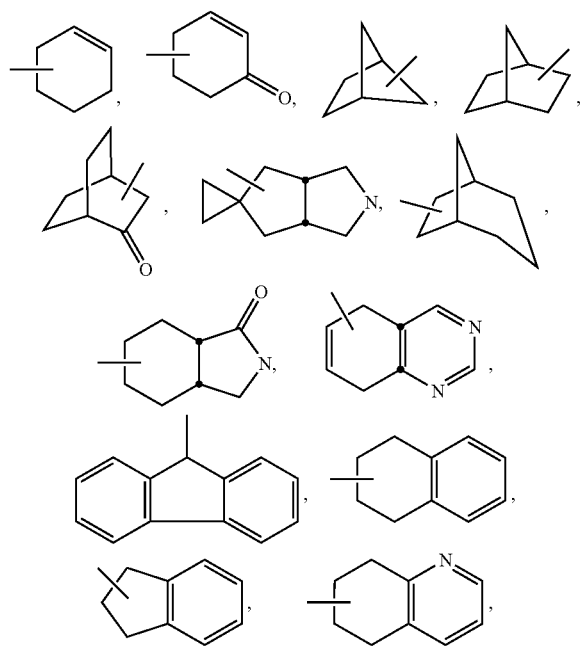

and the like.

The terms "heterocycle," "heterocyclic" and "heterocyclo" refer to fully saturated or partially unsaturated non-aromatic cyclic groups (for example, 4 to 7 membered monocyclic, 7 to 11 membered bicyclic, or 10 to 16 membered tricyclic ring systems) which have at least one heteroatom in at least one carbon atom-containing ring. Each ring of the heterocyclic group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. A heterocyclo ring may have a carbon ring atom replaced with a carbonyl group (C=O), as illustrated above for cycloalkyl groups. The heterocyclic group may be attached to the remainder of the molecule at any nitrogen atom or carbon atom of the ring or ring system. Additionally, the heterocyclo group may have a second or third ring attached thereto in a spiro or fused fashion, provided the point of attachment is to the heterocyclo group. An attached spiro ring may be a carbocyclic or heterocyclic ring and the second and/or third fused ring may be a cycloalkyl, aryl or heteroaryl ring. Exemplary monocyclic heterocyclic groups include azetidinyl, pyrrolidinyl, pyrazolinyl, imidazolidinyl, oxazolidinyl, piperidinyl, piperazinyl, morpholinyl, tetrahydrofuryl, tetrahydropyranyl, thiamorpholinyl, and the like.

Exemplary bicyclic heterocyclic groups include indolinyl, isoindolinyl, quinuclidinyl, benzopyrrolidinyl, benzopyrazolinyl, benzoimidazolidinyl, benzopiperidinyl, benzopiperazinyl, tetrahydroisoquinolinyl, tetrahydroquinolinyl, dihydroisoindolyl and the like.

"Substituted heterocycle," "substituted heterocyclic," and "substituted heterocyclo" refer to heterocycle, heterocyclic or heterocyclo groups substituted with one or more substituents, preferably 1 to 4 substituents, more preferably 1 to 2 substituents, at any available point of attachment to the heterocyclo ring and/or any ring fused or attached thereto in a spiro fashion. Exemplary substituents include, but are not limited to, alkyl, substituted alkyl, and those groups recited above as exemplary substituents for substituted alkyl groups.

The term "heteroaryl" refers to aromatic cyclic groups (for example, 5 to 6 membered monocyclic, 7 to 11 membered bicyclic, or 10 to 16 membered tricyclic ring systems) which have at least one heteroatom in at least one carbon atom-containing ring. Each ring of the heteroaryl group containing a heteroatom may have 1, 2, 3, or 4 heteroatoms selected from nitrogen atoms, oxygen atoms and/or sulfur atoms, where the nitrogen and/or sulfur heteroatoms may optionally be oxidized and the nitrogen heteroatoms may optionally be quaternized. (The term "heteroarylium" refers to a heteroaryl group bearing a quaternary nitrogen atom and thus a positive charge.) The heteroaryl group may be attached to the remainder of the molecule at any nitrogen atom or carbon atom of the ring or ring system. Additionally, the heteroaryl group may have a second or third carbocyclic (cycloalkyl or aryl) or heterocyclic ring fused thereto provided the point of attachment is to the heteroaryl group.

Exemplary monocyclic heteroaryl groups include pyrazolyl, imidazolyl, triazolyl, oxazolyl, furyl, thiazolyl, isoxazolyl, thiazolyl, pyridyl

[i.e., 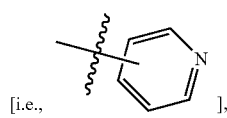 ], pyridazinyl

[i.e., 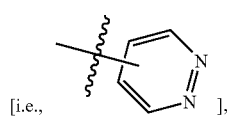 ], pyrimidinyl

[i.e., 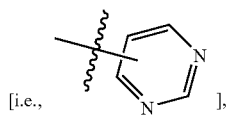], pyrazinyl [i.e., 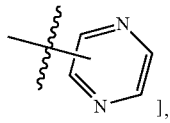], triazinyl, and the like. Unless reference is made to a specific point of attachment, e.g., as in pyrid-2-yl, pyridazin-3-yl, it is intended that such heteroaryl groups can be bonded to another moiety at any available point of attachment.

Exemplary bicyclic heteroaryl groups include benzothiazolyl, benzoxazolyl, benzoxadiazolyl, benzothienyl, quinolinyl, chromenyl, indolyl, indazolyl, isoquinolinyl, benzimidazolyl, benzopyranyl, benzofuryl, benzofurazanyl, benzopyranyl, cinnolinyl, quinoxalinyl, pyrrolopyridyl, furopyridinyl (such as furo[2,3-c]pyridinyl, furo[3,2-b]pyridinyl] or furo[2,3-b]pyridinyl),, triazinylazepinyl, and the like.

"Substituted heteroaryl" refers to heteroaryl groups substituted with one or more substituents as valence allows, preferably 1 to 3 substituents, more preferably 1 to 2 substituents, at any available point of attachment to the heteroaryl ring and/or any ring fused thereto. Exemplary substituents include, but are not limited to, alkyl, substituted alkyl, and those groups recited above as exemplary substituents for substituted alkyl groups.

When reference is made to an optionally-substituted, specifically-named aryl, heteroaryl, cycloalkyl, or heterocyclo ring, the optional substituents may be selected as valence allows from the groups recited above for the genus of rings of which the specifically-named group is a member. For example, "optionally-substituted phenyl" includes unsubstituted phenyl rings as well as phenyl rings containing one or more substituents selected from those recited above for aryl groups. "Optionally-substituted pyridyl, pyridazinyl, pyrimidinyl, and pyrazinyl," includes unsubstituted pyridyl, pyridazinyl, pyrimidinyl, and pyrazinyl rings, as well as such rings containing one or more substituents selected from those recited above for heteroaryl groups.

The term "optionally substituted oxadiazolyl" as used herein is intended to refer to the group,

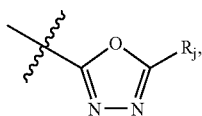

wherein $R_j$ is selected from a substituent recited above for substituted heteroaryl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methylmorpholine-N-oxide, pyridine-N-oxide), and the positively charged nitrogen in an N-amino-ammonium group (e.g., N-aminopyridinium).

The terms "halogen" or "halo" refer to chlorine, bromine, fluorine and/or iodine.

The term haloalkyl refers to an alkyl group having a single halo substituent or multiple halo substituents forming, for example, groups such as a perfluoroalkyl group including trichloromethyl or trifluoromethyl ($CCl_3$ or $CF_3$). A halo$C_1$-$C_4$alkyl refers to a $C_1$-$C_4$alkyl having one or more halo substituents.

The term haloalkoxy refers to an alkoxy group as defined above wherein the alkyl moiety has a single halo substituent or multiple halo substituents forming, for example, groups such as a trifluoromethoxy. A halo$C_1$-$C_4$alkoxy refers to a $C_1$-$C_4$alkoxy having one or more halo substituents.

The term "saturated" when used herein is intended to refer to fully saturated and partially saturated moieties, and conversely, "unsaturated" refers to fully unsaturated and partially unsaturated moieties.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1999).

The term "selective" as used herein with reference to the capability of the claimed compounds to inhibit p38 activity means that the compound in question has a level of activity as measured in enzyme assays for inhibiting the p38 α/β kinase that is significantly greater than the activity of the compound in inhibiting a plurality of other kinases falling within families throughout the human kinome. The term "significantly greater activity" includes the activity of at least one compound having about 500-fold or more greater activity for inhibiting p38α/β enzyme as compared with the activity of the compound in inhibiting other kinases, for example, as compared with the activity of the compound in inhibiting about twenty-five or more other kinases, in another example, as compared with about fifty or more other kinases, and in yet another example, as compared with about 100 or more other kinases. Thus, a selective p38 inhibitor as defined herein according to one embodiment will inhibit the α-isoform of the p38 kinase, the β-isoform of the p38 kinase, and/or both the α and β forms of the p38 kinase, at least 500 times greater than it will inhibit any one of a plurality of other kinases. Thus, for example, considering an embodiment involving comparison with a sample of twenty-five other kinases, p38 selective compounds will have 500 times greater activity in inhibiting p38α/β kinase as compared with any one of each of the twenty-five other kinases considered individually (e.g., in a one-on-one comparison). In another embodiment of the invention, compounds are provided having at least about 1,000-fold greater activity for inhibiting p38 α/β kinase as compared with other kinases, for example, as compared with about twenty-five or more, about fifty or more, and in yet another example, as compared with about 100 or more other kinases. In yet another embodiment of the invention, compounds are provided having at least about 5,000-fold greater activity for inhibiting p38 α/β kinase as compared with other kinases, for example, as compared with about twenty-five or more other kinases, as compared with about fifty or more other kinases, and in yet another example, as compared with about 100 or more other kinases. The term "highly selective" as used herein means the compound in question has at least about 10,000 fold greater activity for inhibiting the p38 α/β kinase enzyme as compared with at least thirty other kinases, more preferably, as compared with at least about fifty or more other kinases. When reference is made herein to "other kinases", applicant intends to refer to kinases known in the field other than the p38 α/β kinases. For example, various known kinases and kinase families other than the 38 α/β kinase are identified in WO 02/062804, and in Manning, G. et al., *The Protein Kinase Complement of the Human Genome, Science* (Washington, D.C., United States) (2002), 198(5600), at pp. 1912-1916, 1933-1934, which is incorporated herein by reference. "Other kinases" as identified therein thus may include, without limitation, one or more kinases chosen from the following kinases and/or kinase families: CaMK1, CaMK2, CDK, DAPK, EMT, FGF, FMS, GSK3, LCK, PDGF-R, PKA, PCK, RAF, RIPK, LIMK-1, SYK, Met, PAK-4, PAK-5, ZC-1, STLK-2, DDR-2, Aurora 1, Aurora 2, Bub-1, PLK, Chk1, Chk2, HER2, JAK, raf1, MEK1, EGF-R, RSK/RSK, IGF-R, IRAK, VEGF-R, P13K, PDK, HIPK, STKR, BRD, Wnk, NKF3, NKF4, NKF5, weel kinase, Src, Abl, ILK, MK-2, IKK-2, RIPK, Cdc7, Ste11, Ste20, Ste7, Tec, Trk, and/or Nek, and so forth. The above is an exemplary, non-limiting list of other kinases. Manning identified 518 protein kinases, and applicant intends to incorporate each one of these 518 protein kinases other than the p38 kinase in the definition of the term "other kinases" as used herein.

There are many enzyme assays known in the field that may be used to measure the levels of activity to determine selectivity. Applicant has described certain enzyme assays below but does not intend to be limited to use of these specific assays with regard to the definition of selectivity herein.

Unless otherwise indicated, a heteroatom with an unsatisfied valence is understood to have hydrogen atoms sufficient to satisfy the valences, as one skilled in the field will appreciate.

The compounds of formula I may form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts may also be useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety, such as but not limited to an amine or a pyridine or imidazole ring, may form salts with a variety of organic and inorganic acids. Exemplary acid addition salts include acetates (such as those formed with acetic acid or trihaloacetic acid, for example, trifluoroacetic acid), adipates, alginates, ascorbates, asparates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochloride, hydrobromides, hydroiodides, hydroxyethanesulfonates (e.g., 2-hydroxyethanesulfonates), lactates, maleates, methanesulfonates, naphthalenesulfonates (e.g., 2-naphthalenesulfonates), nicotinates, nitrates, oxalates, pectinates, persulfates, phenylpropionates (e.g., 3-phenylpropionates), phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety, such as but not limited to a carboxylic acid, may form salts with a variety of organic and inorganic bases. Exemplary basic salts include ammonium salts, alkali metal salts such as sodium, lithium and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glycamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug" as employed herein denotes a compound which, upon administration to a subject, undergoes chemical conversion by metabolic or chemical processes to yield a compound of the formula I, or a salt and/or solvate thereof. Solvates of the compounds of formula I include, for example, hydrates.

Compounds of the formula I, and salts thereof, may exist in their tautomeric form (for example, as an amide or imino ether). All such tautomeric forms are contemplated herein as part of the present invention.

All stereoisomers of the present compounds (for example, those which may exist due to asymmetric carbons on various substituents), including enantiomeric forms and diastereomeric forms, are contemplated within the scope of this invention. Individual stereoisomers of the compounds of the invention may, for example, be substantially free of other isomers (e.g., as a pure or substantially pure optical isomer having a specified activity), or may be admixed, for example, as racemates or with all other, or other selected, stereoisomers. The chiral centers of the present invention may have the S or R configuration as defined by the IUPAC 1974 Recommendations. The racemic forms can be resolved by physical methods, such as, for example, fractional crystallization, separation or crystallization of diastereomeric derivatives or separation by chiral column chromatography. The individual optical isomers can be obtained from the racemates by any suitable method, including without limitation, conventional methods, such as, for example, salt formation with an optically active acid followed by crystallization.

All configurational isomers of the compounds of the present invention are contemplated, either in admixture or in pure or substantially pure form. The definition of compounds of the present invention embraces both cis (Z) and trans (E) alkene isomers, as well as cis and trans isomers of cyclic hydrocarbon or heterocyclo rings.

When reference is made herein to a compound of formula (I) herein, this is intended to refer to each compound of formula (I), and each salt, prodrug, solvate, or isomer thereof, alone or in combination with other compounds of formula (I), other salts, prodrugs, solvates, or isomers of compounds of formula (I), or other compounds not of formula (I), without limitation to the manner in which said compound of formula (I), or salt, prodrug, solvate, or isomer thereof is made or formed, for example, whether existing in a pure form, isolated form, crude form, together with one or more excipients or impurities, existing in a solid or liquid form, in a pharmaceutical preparation before administration to a patient, as formed in the body of a patient after administration to a patient, and so forth.

Throughout the specification, groups and substituents thereof may be chosen to provide stable moieties and compounds.

ALTERNATE EMBODIMENTS

According to one aspect of the invention, there is provided a method of modulating a p38 kinase in a mammal comprising administering to the mammal an amount of a compound of formula (I), effective for inhibiting p38 in a mammal, and there are provided compounds for formula (I), which are advantageous, preferably which are selective, for inhibiting p38 kinase.

One preferred aspect of the invention involves compounds of formula (I),

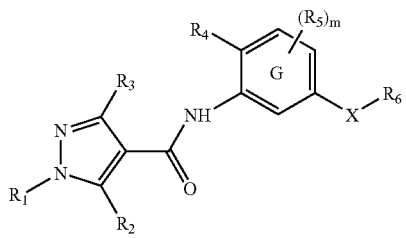

wherein G is phenyl;
$R_1$ is aryl, substituted aryl, heteroaryl, or substituted heteroaryl;
$R_2$ is hydroxyl(alkyl), alkoxy(alkyl), haloalkyl, halogen, cyanoalkyl, alkoxy, substituted alkoxy, or $R_{2a}$, wherein $R_{2a}$ is $C_{1-6}$alkyl, amino, alkylamino, substituted alkylamino, cycloamino, substituted cycloamino, and $C_{1-6}$alkyl substituted with one to two of amino, alkylamino, substituted alkylamino, cycloamino, and/or substituted cycloamino;
$R_3$ is hydrogen or methyl;
$R_4$ is hydrogen, $C_{1-4}$alkyl, halogen, trifluoromethyl, trifluoromethoxy, or cyano;
$R_5$ is trifluoromethyl, trifluoromethoxy, cyano, nitro, alkyl or substituted alkyl;
X is —C(=O)NH—, or is absent;
$R_6$ is hydrogen, alkyl or substituted alkyl, alkoxy or substituted alkoxy, phenoxy or substituted phenoxy, cycloalkyl or substituted cycloalkyl, heterocycle or substituted heterocycle, aryl or substituted aryl, heteroaryl or substituted heteroaryl; or where X is absent, $R_6$ can also be halogen, cyano, trifluoromethyl, alkyl, amino, or alkylamino; or alternatively, $R_6$ is joined together with a group $R_5$ on an adjacent carbon atom to form an optionally-substituted, fused five to six membered heterocyclic or carbocyclic ring; and
m is 0, 1, or 2.

Applicant excludes from the scope of the invention herein as well as from the scope of alternate embodiments of the claimed compounds herein, certain specific species of compounds, namely, (A) compounds having the formula (I), wherein $R_1$ is an optionally-substituted phenyl, pyridyl, pyridazinyl, pyrimidinyl, or pyrazinyl ring; $R_2$ is $R_{2a}$; $R_3$ is hydrogen; $R_4$ is methyl; m is 0; and X—$R_6$ is —C(=O)NH ($C_{1-6}$alkyl), —C(=O)NH(cyclopropyl), or optionally-substituted oxadiazolyl;

(B) compounds having formula (Ix):

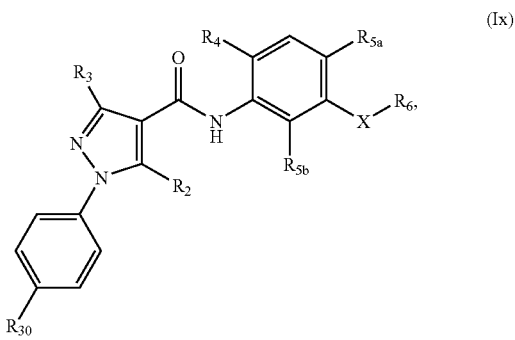

wherein
(i) simultaneously, $R_{30}$ is trifluoromethyl, $R_2$ is methyl, $R_3$ is hydrogen, $R_4$ is bromo, X—$R_6$ is hydrogen, $R_{5b}$ is hydrogen, and $R_{5a}$ is methyl or

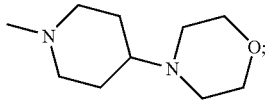

(ii) simultaneously, $R_{30}$ is hydrogen or methoxy, $R_2$ is hydrogen or methyl, $R_3$ is hydrogen, $R_4$ is hydrogen, X—$R_6$ is hydrogen, $R_{5b}$ is hydrogen, and $R_{5a}$ is trifluoromethyl;

(iii) simultaneously, $R_{30}$ is chloro, $R_2$ is hydrogen, $R_3$ is hydrogen, $R_4$ is hydrogen, X—$R_6$ is cyano, $R_{5b}$ is hydrogen, and $R_{5a}$ is $SR_{17}$ wherein $R_{17}$ is morpholinylalkyl;

(iv) simultaneously, $R_{30}$ is fluoro, $R_2$ is methyl, $R_3$ is hydrogen, $R_4$ is hydrogen, X—$R_6$ is cyano, $R_{5b}$ is hydrogen, and $R_{5a}$ is N-piperidinyl;

(v) simultaneously, $R_{30}$ is halogen, $R_2$ is hydrogen or methyl, $R_3$ is hydrogen, $R_4$ is hydrogen, X—$R_6$ is cyano, $R_{5b}$ is hydrogen, and $R_{5a}$ is heterocyclo or substituted heterocyclo;

(vi) simultaneously, $R_{30}$ is chloro, $R_2$ is trifluoromethyl, $R_3$ is hydrogen, $R_4$ is hydrogen, X—$R_6$ is $SO_2NH$ (cycloalkyl), and $R_{5a}$ and $R_{5b}$ are hydrogen;

(vii) simultaneously, $R_{30}$ is hydrogen, $R_2$ is trifluoromethyl, $R_3$ is hydrogen, $R_4$ is hydrogen, X—$R_6$ is hydrogen, $R_{5b}$ is hydrogen, and $R_{5a}$ is substituted alkyl;

(viii) simultaneously, $R_{30}$ is hydrogen, $R_2$ is trifluoromethyl, $R_3$ is hydrogen, $R_4$ is methyl, X—$R_6$ is hydrogen, $R_{5b}$ is —C(=ONH(alkyl), and $R_{5a}$ is hydrogen; and (ix) simultaneously, $R_{30}$ is methoxy, $R_2$ is methyl, $R_3$ is hydrogen, $R_4$ is methyl, X—$R_6$ is a bicycliheterocyclo(alkyl) or bicyclicheteroaryl(alkyl), and $R_{5a}$ and $R_{5b}$ are hydrogen; and (C) compounds having the formula (Iy),

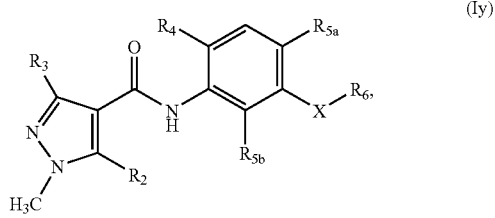

(Iy)

(i) simultaneously, $R_2$ is hydrogen, $R_3$ is trifluoromethyl, $R_4$ is bromo, X—$R_6$ is hydrogen, $R_{5a}$ is trifluoromethyl, and $R_{5b}$ is bromo; and wherein (ii) $R_2$ is methyl, $R_3$ is hydrogen, $R_4$ is hydrogen, X—$R_6$ is cyano, $R_{5a}$ is alkoxy, and $R_{5b}$ is hydrogen.

According to another aspect of the invention, there are provided compounds of formula (I) herein, and methods of administering compounds as defined in formula (I), for modulating the activity of p38 kinase in a patient, and/or for treating p38 associated-conditions in a patient, wherein $R_1$ in formula (I) is selected from:

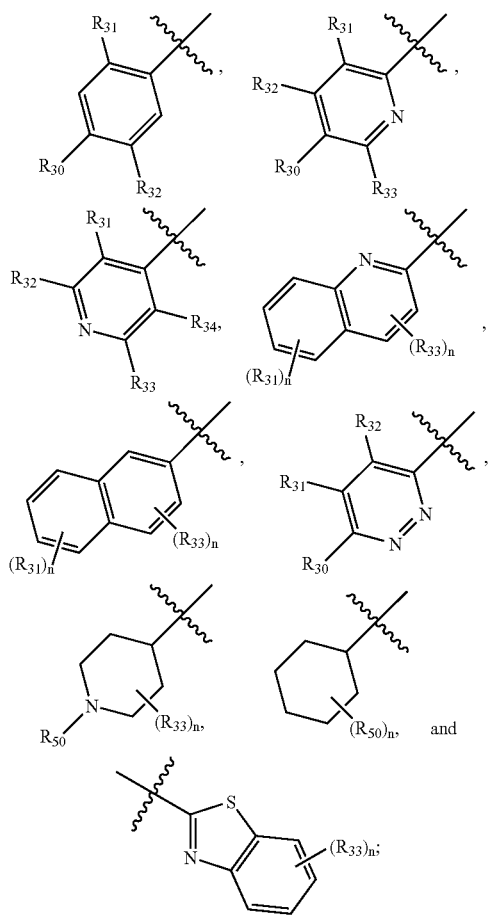

$R_{30}$, $R_{31}$, $R_{32}$, $R_{33}$ and $R_{34}$ are selected from hydrogen, halogen, cyano, trifluoromethyl, trifluoromethoxy, $C_{1-4}$alkyl, O($C_{1-4}$alkyl), nitro, and/or $SO_2CH_3$;

$R_{50}$ is hydrogen, alkyl, or arylalkyl; and n is at each occurrence independently selected from 0-3; and/or pharmaceutically-acceptable salts, prodrugs, solvates, isomers, and/or hydrates thereof.

According to another aspect of the invention, there are provided compounds of formula (I) herein, and methods of administering compounds as defined in formula (I), for modulating the activity of p38 kinase in a patient, and/or for treating p38 associated-conditions in a patient, wherein:

$R_1$ is optionally-substituted aryl or heteroaryl;

$R_2$ is hydrogen, lower alkyl, halogen, haloalkyl, trifluoromethyl, $NH_2$, NH(alkyl), NH(cycloalkyl), N(alkyl)$_2$, or —CH$_2$—O—CH$_3$, wherein each of said alkyl and/or cycloalkyl groups of $R_2$ are in turn optionally substituted with one to two of hydroxy, alkoxy, heteroaryl, aryl, heterocyclo, cycloalkyl, amino, and alkylamino;

$R_3$ is hydrogen or methyl;

$R_4$ is methyl or halogen;

X is —C(=O)NH— or is absent;

$R_6$ is lower alkyl or cyclopropyl, or when X is absent, $R_6$ is optionally-substituted heteroaryl; and m is 0 or 1; and/or pharmaceutically-acceptable salts, prodrugs, solvates, isomers, and/or hydrates thereof.

According to another aspect of the invention, there are provided compounds, and methods of administering compounds for modulating the activity of p38 kinase in a patient, and/or for treating p38 associated-conditions in a patient, wherein the compounds having the formula (I), above, wherein:

$R_1$ is optionally-substituted phenyl or pyridyl; and $R_2$ is hydrogen, lower alkyl, halogen, haloalkyl, trifluoromethyl, $NH_2$, NH(alkyl), NH(cycloalkyl), N(alkyl)$_2$, or —CH$_2$—O—CH$_3$, wherein each of said alkyl groups of NH(alkyl), and/or N(alkyl)$_2$, are in turn optionally substituted with one to two of OH, O($C_{1-4}$alkyl), imidazolyl, pyridyl, phenyl, tetrahydrofuryl, $NH_2$, NH(alkyl), N(alkyl)$_2$, and/or N-morpholinyl.

According to another aspect of the invention, there are provided compounds, and methods of administering compounds for modulating the activity of p38 kinase in a patient, and/or for treating p38 associated-conditions in a patient, wherein the compounds having the formula (I), above, wherein:

$R_3$ is hydrogen or methyl;

$R_4$ is methyl or halogen;

X is —C(=O)NH— or is absent;

$R_6$ is lower alkyl or cyclopropyl, or when X is absent, $R_6$ is optionally-substituted heteroaryl; and m is 0 or 1; and/or pharmaceutically-acceptable salts, prodrugs, solvates, isomers, and/or hydrates thereof.

According to another aspect of the invention, there are provided compounds, and methods of administering compounds for modulating the activity of p38 kinase in a patient, and/or for treating p38 associated-conditions in a patient, wherein the compounds having the formula (I), above, wherein:

$R_1$ is optionally-substituted phenyl or pyridyl;

$R_2$ is hydrogen, lower alkyl, halogen, haloalkyl, trifluoromethyl, $NH_2$, NH(alkyl), NH(cycloalkyl), N(alkyl)$_2$, or —CH$_2$—O—CH$_3$, wherein each of said alkyl groups of NH(alkyl), and/or N(alkyl)$_2$, are in turn optionally substituted with one to two of OH, O($C_{1-4}$alkyl), imidazolyl, pyridyl, phenyl, tetrahydrofuryl, $NH_2$, NH(alkyl), N(alkyl)$_2$, and/or N-morpholinyl;

R₃ is hydrogen or methyl (more preferably hydrogen);
R₄ is methyl or halogen (more preferably methyl);
X is —C(=O)NH— or is absent;
R₆ is lower alkyl or cyclopropyl, or when X is absent, R₆ is optionally-substituted heteroaryl; and
m is 0; and/or pharmaceutically-acceptable salts, prodrugs, solvates, isomers, and/or hydrates thereof.

According to another aspect of the invention, there are provided compounds, and methods of administering compounds for modulating the activity of p38 kinase in a patient, and/or for treating p38 associated-conditions in a patient, wherein the compounds having the formula (I), above, wherein:

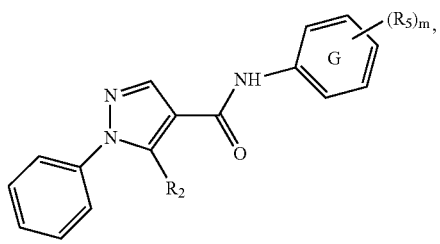

wherein G is phyenyl or pyridyl, R₅ is halogen, hydroxyl, alkoxy, $C_{1-4}$alkyl, halo$C_{1-4}$alkyl, cyano, $SO_2(C_{1-4}$alkyl), nitro, heteroaryl, substituted heteroaryl, —C(=O)NH(alkyl), —C(=O)NH₂, and/or —C(=O)NH(cycloalkyl); wherein m is 0, 1, or 2; and/or pharmaceutically-acceptable salts, prodrugs, solvates, isomers, and/or hydrates thereof; excluding the specifically-identified compounds and groups of compounds excluded from the scope of formula (I), above.

According to another aspect of the invention, there are provided compounds, and methods of administering compounds for modulating the activity of p38 kinase in a patient, and/or for treating p38 associated-conditions in a patient, wherein the compounds having the formula (I), above, R₃ is hydrogen and R₄ is methyl.

According to another aspect of the invention, there are provided compounds, and methods of administering compounds for modulating the activity of p38 kinase in a patient, and/or for treating p38 associated-conditions in a patient, wherein the compounds having the formula (I), above, wherein G is phenyl and R₆ is a 5-membered heteroaryl which may be optionally substituted.

According to another aspect of the invention, there are provided compounds, and methods of administering compounds for modulating the activity of p38 kinase in a patient, and/or for treating p38 associated-conditions in a patient, wherein the compounds having the formula (I), above, wherein R₆ is selected from the group consisting of:

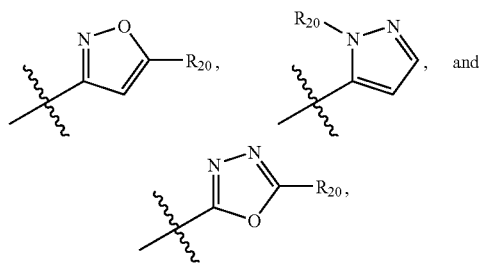

wherein R₂₀ is hydrogen, lower alkyl, $C_{3-6}$cycloalkyl, or phenyl, more preferably wherein R₂₀ is methyl or ethyl.

According to another aspect of the invention, there are provided compounds, and methods of administering compounds for modulating the activity of p38 kinase in a patient, and/or for treating p38 associated-conditions in a patient, wherein the compounds having the formula (I), above, wherein R₆ is selected from one of the heteroaryl groups recited immediately above, wherein X is absent or —C(=ONH—.

According to yet another aspect of the invention, there are provided compounds according to the formula (I), above, wherein the various groups are as recited above for formula (I), but excluding (A) compounds having the formula (I), wherein R₁ is an optionally-substituted phenyl, pyridyl, pyridazinyl, pyrimidinyl, or pyrazinyl ring; R₂ is R₂ₐ; R₃ is hydrogen; R₄ is methyl; m is 0; and X—R₆ is —C(=O)NH ($C_{1-6}$alkyl), —C(=O)NH(cyclopropyl), or optionally-substituted oxadiazolyl;

(B) compounds having formula (Ix):

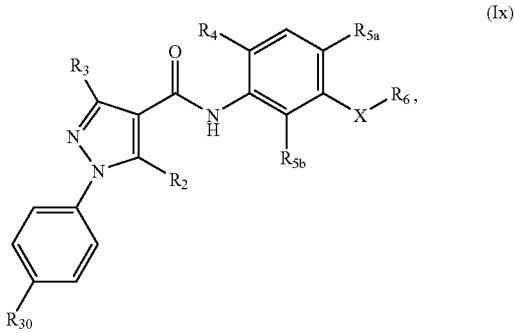

wherein, simultaneously
(i) R₃₀ is selected from hydrogen, trifluoromethyl, halogen, and methoxy;
(ii) R₂ is selected from hydrogen, methyl, and trifluoromethyl;
(iii) R₃ is hydrogen;
(iv) R₄ is selected from hydrogen, bromo, and lower alkyl;
(v) X—R₆ is selected from hydrogen, cyano, SO₂NH(cycloalkyl), bicyclicheterocyclo(alkyl) and bicylicheteroaryl(alkyl);
(vi) R₅ᵦ is selected from hydrogen and —C(=ONH (alkyl); and
(vii) R₅ₐ is selected from hydrogen, alkyl, substituted alkyl, heterocyclo, or substituted heterocyclo, trifluoromethyl, and SR₁₇ wherein R₁₇ is morpholinylalkyl;
X—R₆ is a, and R₅ₐ and R₅ᵦ are hydrogen; and
(C) compounds having the formula (Iy),

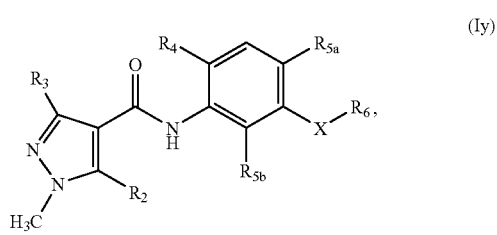

wherein
(i) simultaneously, $R_2$ is hydrogen or methyl, $R_3$ is hydrogen or trifluoromethyl, $R_4$ is hydrogen or bromo, X—$R_6$ is hydrogen or cyano, $R_{5a}$ is trifluoromethyl or alkoxy, and $R_{5b}$ is hydrogen or bromo.

Various combinations of groups recited above may be selected to form further preferred and/or alternate embodiments of the invention. Additionally, other aspects of the invention may be apparent to one skilled in the field considering the entire disclosure hereof, including the definitions, schemes, claims and examples herein.

METHODS OF PREPARATION

Compounds of Formula (I) may be prepared according to the following Schemes and the knowledge of one skilled in the art. Variables set forth in the schemes, e.g., $R_1$ through $R_8$, can be selected from those groups recited in the claims herein, and Q may be selected from $R_1$ in the claims. Solvents, temperatures, pressures, and other reaction conditions may readily be selected by one of ordinary skill in the art.

under standard amine coupling conditions. Alternatively, the carboxylic acid moiety of (1-2) can be converted to the acid chloride (1-3), which reacts directly with (1-4) in solvents such as DCM in the presence of DIPEA (or other bases) to afford (Ia).

Scheme 1a

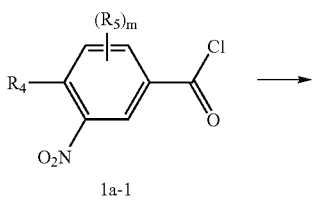

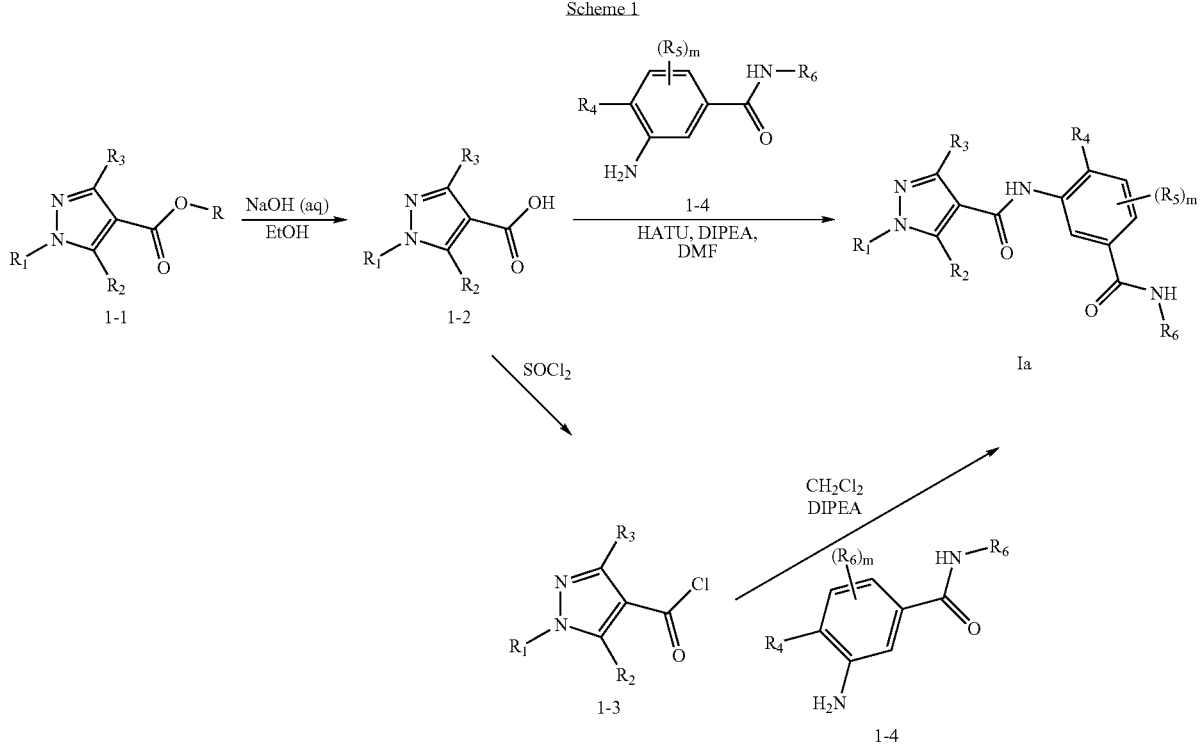

Compounds of formula (I) having the structure (Ia) can be prepared according to Scheme 1. Substituted pyrazoles (1-1) are either commercially available or can be prepared according to literature procedures. See, e.g., Europ. J. Org. Chem., 17, 2913-2920 (2002); WO 01/46172; Heterocycles, 53, 2775-2780 (2000); J. Heterocyclic Chem., 37, 175-180 (2000); Nippon Kagaku Kaishi, 10, 1144-1147 (1992); Pakistan J. Scientific and Industrial Research, 30, 1-4 (1987); J. Heterocyclic Chem., 16, 657-660 (1979); J. Org. Chem., 21, 1240 (1956); and Joule et al., Heterocyclic Chemistry, 3d edition, Chapter 22. Hydrolysis of (1-1) gives the corresponding pyrazole acids (1-2), which can be coupled with aniline (1-4) or its salt form (such as HCl) to give compounds (Ia)

-continued

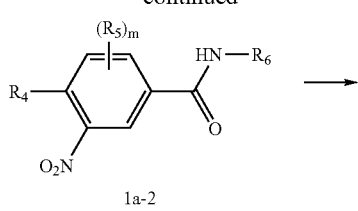

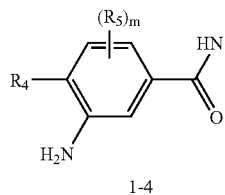

1-4

Compound (1-4) can be prepared as outlined in Scheme 1a by 1) reacting a 3-nitro-benzoyl chloride (1a-1) (either commercially available or can be prepared by one skilled in the art) and an amine $H_2N$—$R_6$ in $CH_2Cl_2$ to give a nitro intermediate (1a-2); and 2) reducing (1a-2) under conditions such as hydrogen gas and a catalyst in a solvent to afford aniline (1-4). Its salt form can be prepared by reacting (1-4) with an appropriate acid (e.g., HCl).

Scheme 1b

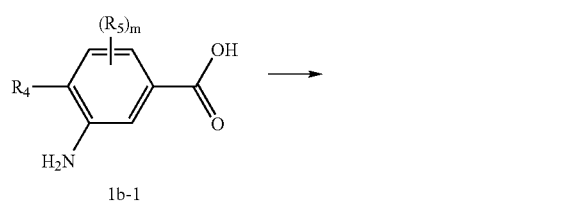

1b-1

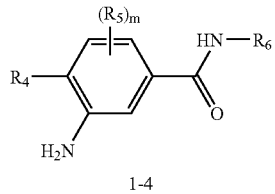

1-4

Alternatively, Compound (1-4) can be prepared as outlined in Scheme 1b, by reacting a 3-amino-benzoic acid (1b-1) (either commercially available or can be prepared by one skilled in the art) with the amine $H_2N$—$R_6$ in the presence of a coupling agent, such as EDC/HOBt, in a suitable solvent. Its salt form can be prepared by reacting (1-4) with an appropriate acid (e.g., HCl).

Scheme 2

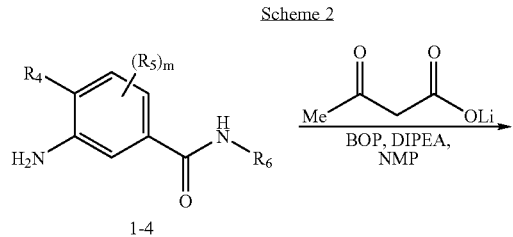

1-4

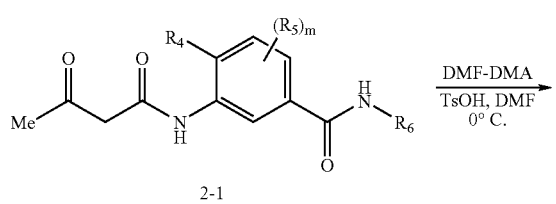

2-1

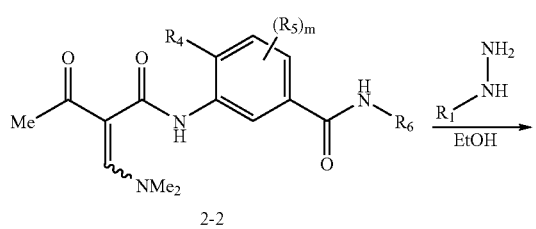

2-2

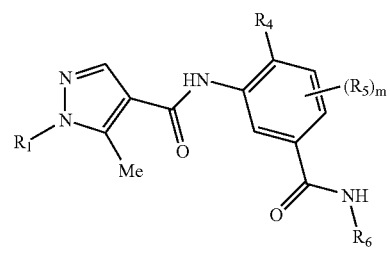

2-3

The compound of formula (I) having the structure (2-3) can be made through the alternate route outlined in Scheme 2. BOP coupling of aniline (1-4) with lithium acetoacctate gives compound (2-1), which can be reacted with DMF-DMA to give compound (2-2). Compound (2-2) can then be reacted with hydrazines to afford compound (2-3).

Scheme 3

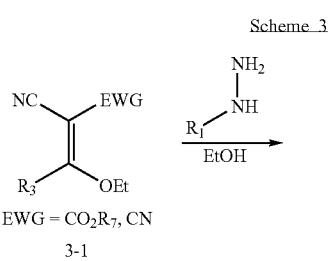

EWG = $CO_2R_7$, CN 3-1

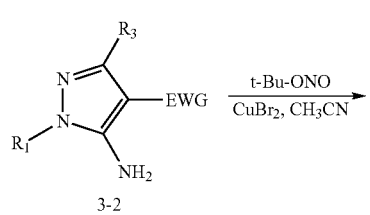

3-2

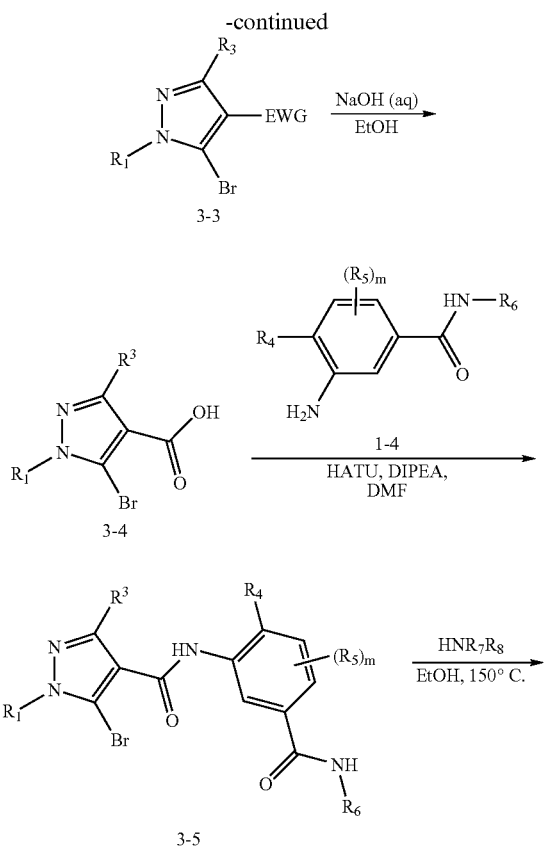

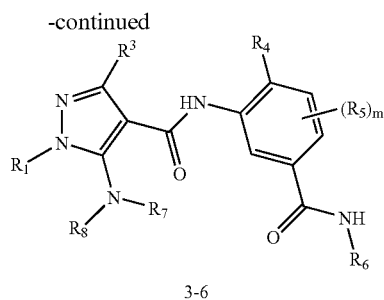

Pyrazoles bearing halo, amino, or alkylamino substitution at C5 can be prepared according to Scheme 3. Reaction of compound (3-1) (such as 2-ethoxymethylene-malononitrile or 2-cyano-3-ethoxy-acrylic acid ethyl ester) with hydrazines gives pyrazoles (3-2), where the C4 position is substituted by a electron withdrawing group (EWG) such as nitrile, methyl or ethyl ester. Conversion of the C5-amino group to the C5-bromo group can be accomplished through reaction with tBuONO and copper (II) bromide. Hydrolysis of the ester or nitrile to the carboxylic acid, followed by amide bond formation, such as through reaction with HATU and the aniline (1-4), gives compound (3-5). Substitution of the bromide with nucleophiles (carbon, oxygen, sulfur, but in particular nitrogen-based nucleophiles) can be accomplished. Reaction of compounds (3-5) with primary or secondary amines in EtOH at elevated temperature and pressure, under microwave irradiation gives amino-substituted pyrazoles (3-6).

Scheme 4

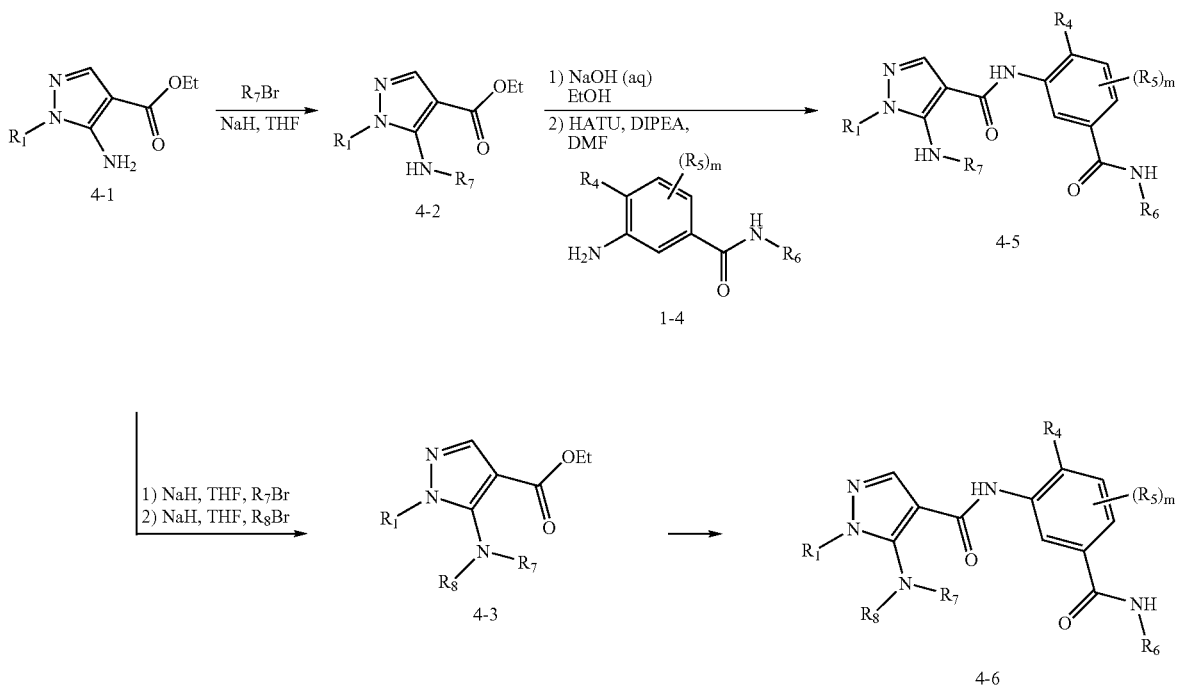

C5-amino substituted pyrazoles can alternately be prepared as shown in Scheme 4. Aminopyrazoles (4-1) (generally prepared according to Scheme 3) can be mono- or bisalkylated through the reaction with alkyl halides (such as ethyl bromide) in the presence of a suitable base (such as NaH) to afford (4-2) or (4-3). Hydrolysis of the ester, followed by amide bond formation, such as through HATU coupling with (1-4), leads to the C5-alkylamino substituted pyrazoles (4-5) or (4-6).

organic solvent, such as DCE, in the presence of a base, such as triethylamine, to afford compound (5-2). Compound (5-2) can reacted with an acid, such as TFA, and neutralized with a base, such as aqueous sodium carbonate, to afford compound (5-3). Formation of the oxadiazole can be accomplished by heating compound (5-3) in triethyl orthoacetate to afford compound (5-4) that can be reduced with hydrogen in the presence of a suitable catalyst, such as palladium on carbon, in a solvent, such as EtOH, to afford compound (5-5). Compound (5-5) can then be coupled to carboxylic acid (6) in a solvent such as DMF to provide compound (Ig). It should be understood from the foregoing that in Shemes 1-4 and 6-8 herein, the oxadiazolyl-substituted aniline compound of formula (5-5) can be substituted for the aniline of formula (1-4) and reacted with carboxylic acid pyrazoles, as in Schemes 1, 3 and 4, and/or treated as shown in the Schemes 2 and 8, to provide compounds of formula (I) and/or precursors thereof.

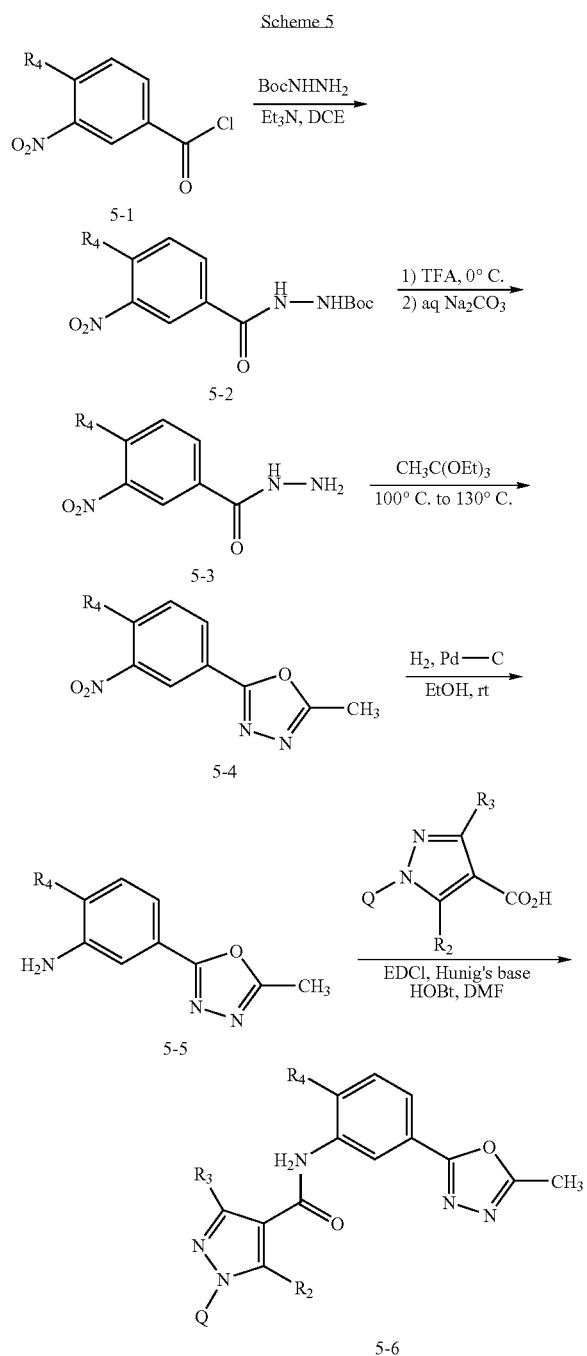

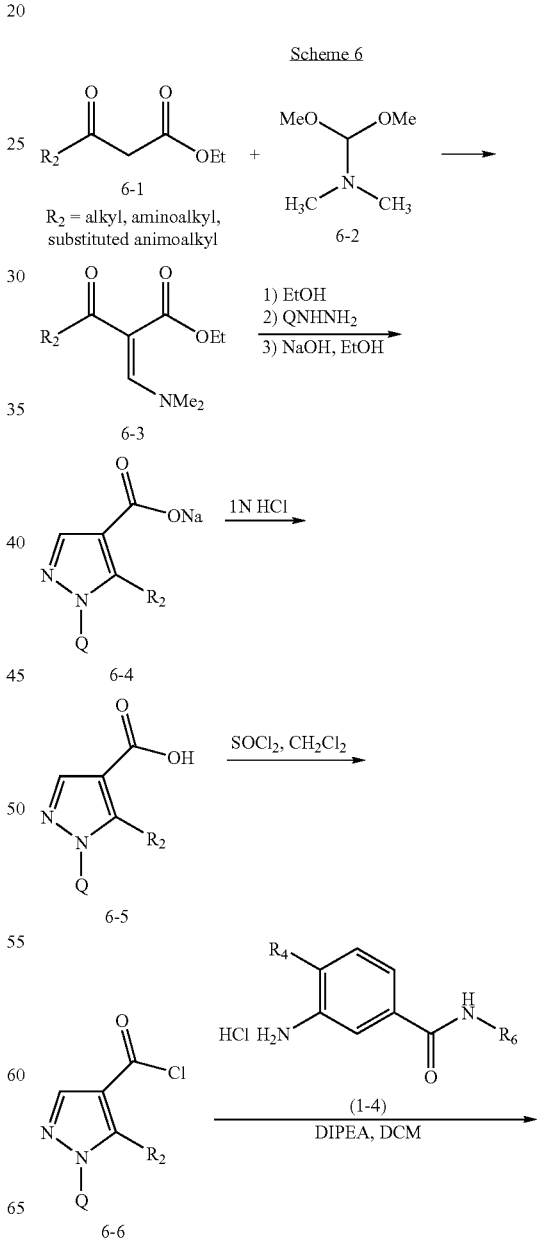

Compounds of formula (5-6) can be prepared from commercially-available compound (5-1) as depicted in Scheme 5. Compound (5-1) can be reacted with tert-butyl carbazate in an

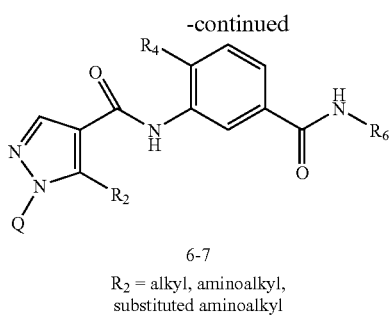

6-7

R₂ = alkyl, aminoalkyl, substituted aminoalkyl

Scheme 6 shows a process for making compounds of formula (6-7), wherein R₂ is alkyl, aminoalkyl, or substituted aminoalkyl. Ethylacetoacetate (6-1), for example, ethyl 3-oxobutanoate, can be reacted with methanamine, such as dimethoxy-N-N-dimethylmethanamine (6-2) in solvent to provide intermediate compound (6-3), which when reacted with an appropriate hydrazine, such as, for example, phenylhydrazine, pyridylhydrazine, etc., followed by addition of sodium hydroxide, provides intermediate sodium salt of formula (6-4). Reaction of sodium salt with acid such as HCl provides carboxylic acid of formula (6-5). The carboxylic acid can then be converted to the acid chloride upon reaction with sulfuryl chloride (see also scheme 1), in solvents such as DCM to provide compounds (6-6), which react with benzamide hydrochloride (1-4) (or alternatively compounds 5-5 as in scheme 5), in solvents such as DCM in the presence of base such as DIPEA to provide compounds having the formula (6-7).

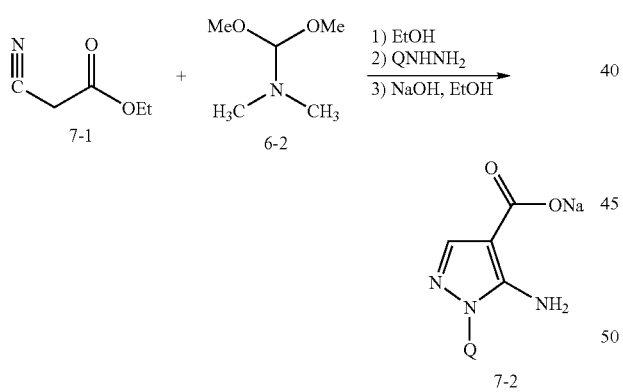

Scheme 7 reflects an alternate process following the general schematic of Scheme 6, but wherein R₂ is a directly-linked amine group, i.e., cyano compound 7-1 is reacted with methanamine, such as dimethoxy-N-N-dimethylmethanamine (6-2) in solvent, followed by an appropriate hydrazine, such as, for example, phenylhydrazine, pyridylhydrazine, etc., in solvent, such as ethanol, followed by addition of sodium hydroxide, to provides intermediate sodium salt of formula (7-2). The amino group of compound (7-2) which can be further elaborated to an alkylamine or substituted amine group R₂, applying principles known in the field, and/or compound (7-2) can be incorporated into other schemes and processes disclosed herein. One skilled in the field will appreciate whether use of amine-protecting groups for the amine of compound (7-2) may be appropriate given other reagents.

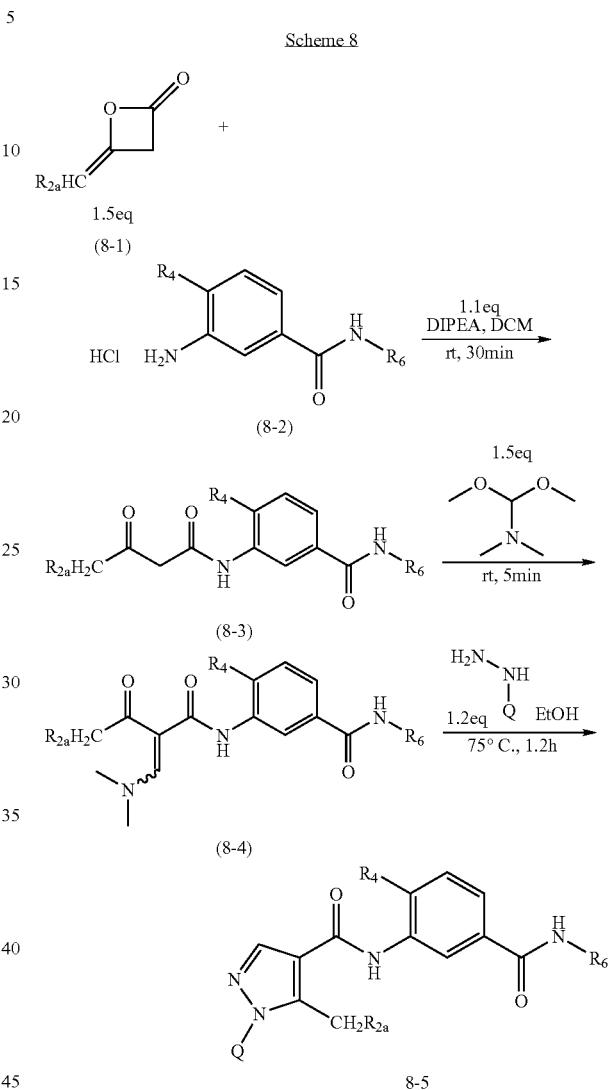

Diketene (8-1), wherein R$_{2a}$ is hydrogen, alkyl, cycloamino, aminoalkyl (preferably wherein R$_{2a}$ is hydrogen), and 3-amino-N-cyclopropyl-4-methylbenzamide hydrochloride can be reacted with DIPEA in DCM at RT to provide compounds (8-3). Addition of DMF-DMA at RT and removal of DCM provides compounds (8-4), which upon reaction with appropriate hydrazine (QNHNH₂), such as optionally-substituted phenylhydrazine, pyridylhydrazine, etc., in solvent such as EtOH, provides compounds of formula (8-5) wherein R$_{2a}$ is as defined above, preferably hydrogen.

In addition, other compounds of formula (I) may be prepared using procedures generally known to those skilled in the art. In particular, the following examples provide additional methods for the preparation of the compounds of this invention.

The invention will now be further described by the following working examples, which are preferred embodiments of the invention. HPLC purifications were done on C18 reverse phase (RP) columns using water MeOH mixtures and TFA as buffer solution. These examples are illustrative rather than Example 1

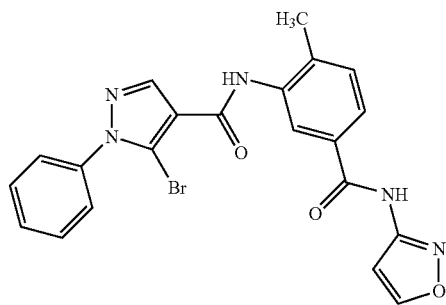

Step A:

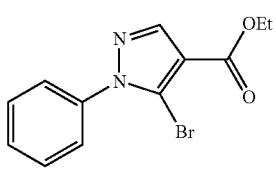
(1A)

To a solution 5-amino-1-phenyl-1H-pyrazole-4-carboxylic acid ethyl ester (0.25 g, 1.05 mmol) and copper (II) bromide (0.281 g, 1.26 mmol) in acetonitrile (2 mL) at 0° C. was added tert-butylnitrite (0.167 mL, 1.26 mmol) dropwise. The reaction was warmed to RT over 2 hr, then stirred overnight at RT. The reaction was layered with EtOAC (8 mL) and washed with 1N aq. HCl (2×3 mL), water (1×3 mL), brine (1×3 mL). The organic phase was dried over MgSO$_4$, filtered, and evaporated to afford (1A) as a yellow solid (0.304 g, 98%, 85% AP HPLC). HPLC ret. t. (min): 3.62, MW: 295.13, LCMS[M+H]$^+$=295.3.

Step B:

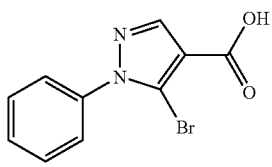
(1B)

To a solution of compound (1A) (0.025 g, 0.085 mmol) in THF (1 mL) at 0° C. was added aq. NaOH (1 N, 0.25 mL, 0.25 mmol). The solution was warmed to RT overnight, then heated to 50° C. for 3-4 hr. The THF was evaporated and the aqueous solution was acidified to approximately pH 3. The resulting precipitate was collected by filtration and allowed to air dry, affording (1B) as an off-white solid (0.015 g, 64%) HPLC ret. t. (min): 2.54, LCMS[M+H]$^+$=267.1, 269.1.

Step C:

To 5-bromo-1-phenyl-1H-pyrazole-4-carboxylic acid (1B) (0.25 g, 0.936 mmol) was added thionyl chloride (3 mL). After stirring at RT for 1 hr, the thionyl chloride was evaporated. The resulting solid was re-suspended in DCM (4 mL) and DIPEA (0.652 mL, 3.74 mmoL) and 3-Amino-N-isoxazol-3-yl-4-methyl-benzamide (0.224 g, 1.03 mmol) were added. The reaction was stirred at RT overnight. The resulting solid that formed was collected by filtration and washed with DCM to afford Example 1 as a yellow solid (0.415 g, 95%). HPLC ret. t. (min): 2.97, MW: 466.3, LCMS[M+H]$^+$=466.1.

Examples 2-45

Compounds having the formula immediately below, wherein $R_1$, $R_2$, and $R_6$ have the values reported in Table 1, were prepared following an analogous procedure as described for Example 1.

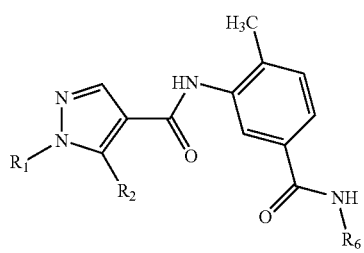
(Ia)

TABLE 1

| Ex. No. | $R_1$ | $R_2$ | $R_6$ | HPLC time (min.) | MS (M$^+$) |
|---|---|---|---|---|---|
| 2 | *piperidine-N-benzyl at 4-position* | —CH$_3$ | *cyclopropyl* | 2.05 | 472.3 |

TABLE 1-continued

| Ex. No. | R₁ | R₂ | R₆ | HPLC time (min.) | MS (M⁺) |
|---|---|---|---|---|---|
| 3 | (S)-2-hydroxybutyl | —CH₃ | cyclopropyl | 2.05 | 371.3 |
| 4 | cyclohexyl | —CH₃ | isoxazol-3-yl | 3.10 | 408.1 |
| 5 | benzyl | —CH₃ | isoxazol-3-yl | 2.92 | 416.0 |
| 6 | n-butyl | —CH₃ | isoxazol-3-yl | 2.89 | 382.1 |
| 7 | n-propyl | —CH₃ | isoxazol-3-yl | 3.08 | 381.2 |
| 8 | benzyl | —CH₃ | cyclopropyl | 2.87 | 389.2 |
| 9 | n-butyl | —CH₃ | cyclopropyl | 2.82 | 355.2 |
| 10 | 6-ethoxypyridazin-3-yl | —CH₃ | isoxazol-3-yl | 2.91 | 448.2 |
| 11 | quinolin-2-yl | —CH₃ | isoxazol-3-yl | 3.35 | 453.1 |

TABLE 1-continued
| Ex. No. | R₁ | R₂ | R₆ | HPLC time (min.) | MS (M⁺) |
|---|---|---|---|---|---|
| 12 | 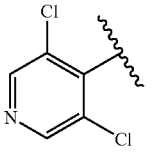 | —CH₃ | 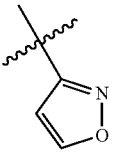 | 2.83 | 471.1 |
| 13 | 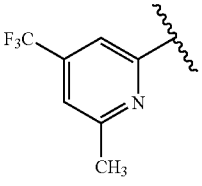 | —CH₃ | 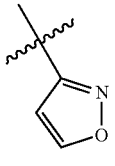 | 3.52 | 485.1 |
| 14 | 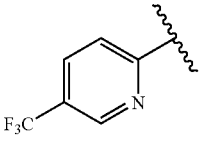 | —CH₃ | 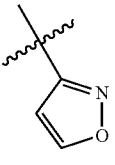 | 3.42 | 471.1 |
| 15 | 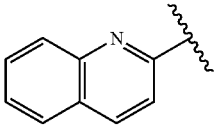 | —CH₃ | 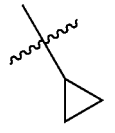 | 3.30 | 426.1 |
| 16 | 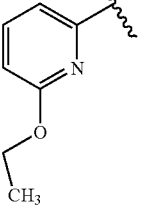 | —CH₃ | 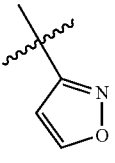 | 3.34 | 447.1 |
| 17 | 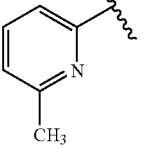 | —CH₃ | 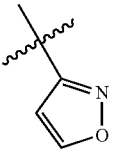 | 2.82 | 417.1 |
| 18 | 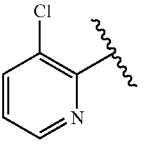 | —CH₃ | 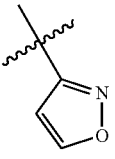 | 2.61 | 437.1 |
| 19 | 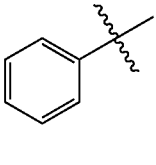 | 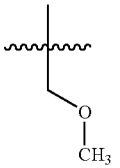 | 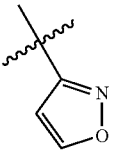 | 2.97 | 432.1 |

TABLE 1-continued

| Ex. No. | R₁ | R₂ | R₆ | HPLC time (min.) | MS (M⁺) |
|---|---|---|---|---|---|
| 20 | phenyl | -CH₂-O-CH₃ | cyclopropyl | 2.90 | 404.2 |
| 21 | phenyl | H | cyclopropyl | 2.82 | 361.2 |
| 22 | —CH₃ | —CF₃ | cyclopropyl | 2.44 | 367.0 |
| 23 | phenyl | —CF₃ | cyclopropyl | 3.02 | 429.3 |
| 24 | phenyl | -CH₂CH₂CH₃ | isoxazol-3-yl | 3.15 | 430.2 |
| 25 | phenyl | -CH₂CH₂CH₃ | cyclopropyl | 3.24 | 403.3 |
| 26 | pyridin-3-yl | —CH₃ | cyclopropyl | 2.19 | 376.1 |
| 27 | pyridin-3-yl | —CH₃ | isoxazol-3-yl | 2.33 | 403.1 |
| 28 | 3-(methylsulfonyl)phenyl | —CH₃ | isoxazol-3-yl | 2.47 | 480.1 |

TABLE 1-continued
| Ex. No. | R₁ | R₂ | R₆ | HPLC time (min.) | MS (M⁺) |
|---|---|---|---|---|---|
| 29 | 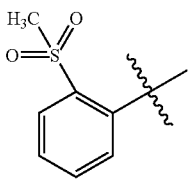 | —CH₃ | 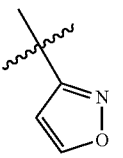 | 2.50 | 480.1 |
| 30 | 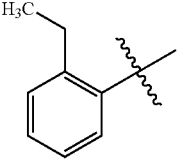 | —CH₃ | 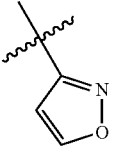 | 3.15 | 430.1 |
| 31 | 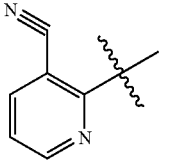 | —CH₃ | 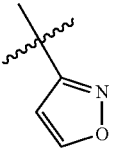 | 2.30 | 428.1 |
| 32 | 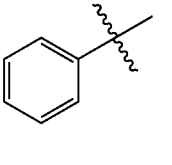 | —CH₃ | 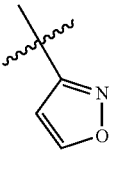 | 2.93 | 402.1 |
| 33 | 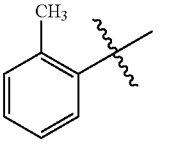 | —CH₃ | 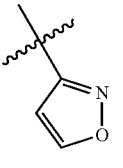 | 3.12 | 416.1 |
| 34 | 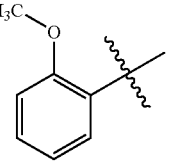 | —CH₃ | 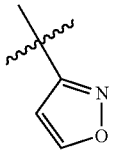 | 2.63 | 432.1 |
| 35 | 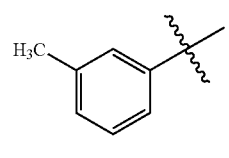 | —CH₃ | 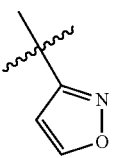 | 3.14 | 416.0 |
| 36 | 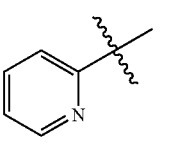 | —CH₃ | 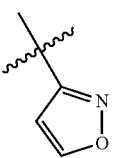 | 2.64 | 403.1 |

TABLE 1-continued

| Ex. No. | R₁ | R₂ | R₆ | HPLC time (min.) | MS (M⁺) |
|---|---|---|---|---|---|
| 37 | benzothiazol-2-yl | —CH₃ | isoxazol-3-yl | 3.65 | 459.1 |
| 38 | benzothiazol-2-yl | —CH₃ | cyclopropyl | 3.63 | 432.1 |
| 39 | 2,6-dichlorophenyl | —CH₃ | isoxazol-3-yl | 3.03 | 470.1 |
| 40 | phenyl | n-propyl | 1H-pyrazol-3-yl | 3.02 | 429.1 |
| 41 | phenyl | n-propyl | 1-methyl-pyrazol-5-yl | 3.13 | 443.1 |
| 42 | phenyl | n-propyl | 1-ethyl-pyrazol-5-yl | 3.18 | 457.1 |
| 43 | phenyl | n-propyl | 1-phenyl-pyrazol-5-yl | 3.34 | 505.1 |
| 44 | (1H-pyrazol-4-yl)carbonyl | —H | cyclopropyl | 2.49 | 379.2 |

TABLE 1-continued

| Ex. No. | R₁ | R₂ | R₆ | HPLC time (min.) | MS (M⁺) |
|---|---|---|---|---|---|
| 45 | —H | —H | cyclopropyl | 1.75 | 285.2 |
| 46 | naphthyl | —CH₃ | cyclopropyl | 3.22 | 425.2 |
| 47 | tert-butyl | —CH₃ | cyclopropyl | 2.73 | 355.3 |

Examples 48-49

Compounds having the formula immediately below, wherein $R_1$, $R_2$, and $R_6$ have the values reported in Table 2, were prepared following an analogous procedure as described for Example 1.

TABLE 2

| Ex. No. | R₁ | R₂ | R₆ | HPLC time (min.) | MS (M⁺) |
|---|---|---|---|---|---|
| 48 | —CH₃ | —CH₃ | isoxazolyl | 2.25 | 354.1 |
| 49 | —CH₃ | —CH₃ | cyclopropyl | 2.10 | 327.1 |

Example 50

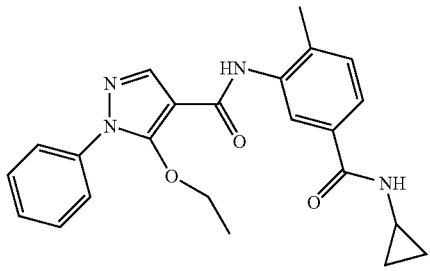

Step A:

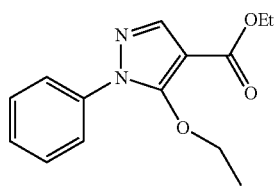

(50A)

To a solution of 5-bromo-1-phenyl-1H-pyrazole-4-carboxylic acid ethyl ester (0.050 g, 0.169 mmol) in EtOH (1 mL) was added NaOEt (21 wt %, 0.190 mL, 0.50 mmol). The solution was heated to 80° C. for 1.5 hr, then the EtOH was evaporated. The residue was taken up in water (2 mL), and extracted with EtOAc (3×3 mL). The extracts were washed with brine, dried over MgSO₄, filtered and concentrated to afford (50A) (0.0093 g, 21%). HPLC ret. t. (min): 3.34, MW: 360.3, LCMS[M+H]⁺=261.

Step B:

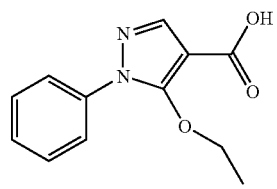

(50B)

To a solution of (50A) (0.009 g, 0.035 mmol) in THF (2 mL) was added aq. NaOH (1 N, 0.140 mL, 0.140 mmol). The reaction was stirred at RT for 2 h, then heated to 50° C. and stirred overnight. The THF was evaporated, additional NaOH (0.50 mL) was added and heating continued for an additional 24 hr. The solution was acidified to pH2-3 and extracted with EtOAc. The extracts were washed with brine, dried over MgSO₄, filtered and concentrated to afford (50B) (0.009 g, (90% AP)) The material was used without further purification. HPLC ret. t. (min): 2.69, MW: 232.2, LCMS[M+H]$^+$=233.

Step C:

To a solution of (50B) (0.009 g, 0.035 mmol) in DMF (1 mL) was added HATU (0.025 g, 0.056 mmol) and DIPEA (0.030 mL, 0.172 mmol). After stirring at RT for 45 min., 3-Amino-N-cyclopropyl-4-methyl-benzamide hydrochloride (0.013 g, 0.056 mmol) was added. The reaction was stirred at RT overnight, then heated to 65° C. for 5 hr. Water (2 mL) was added and the product was extracted with ethyl acetate to afford a crude residue that was further purified by Prep HPLC to afford (50) an off-white solid (0.0051 g, 36% over 2 steps). HPLC ret. t. (min): 2.90, MW: 404.5, LCMS [M+H]$^+$=405.1.

Examples 51-116

The following examples shown in Table 3 were prepared in a manner analogous to Examples 1 and 50.

TABLE 3

| Ex. No. | Structure | HPLC time (min.) | MS (M$^+$) |
|---|---|---|---|
| 51 | 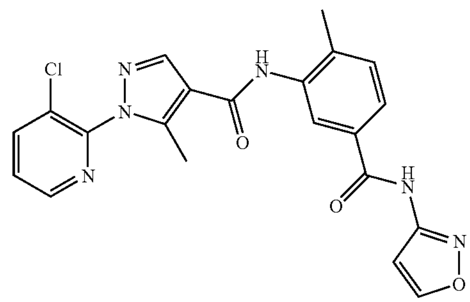 | 2.61 | 437.1 |
| 52 | 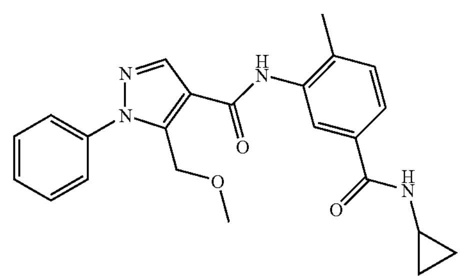 | 2.90 | 404.2 |
| 53 | 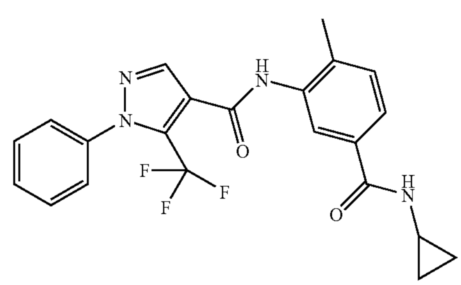 | 3.02 | 429.3 |
| 54 | 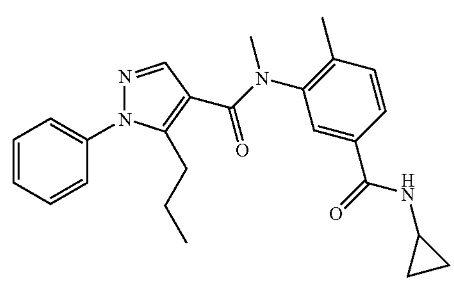 | 3.12 | 417.2 |

TABLE 3-continued
| Ex. No. | Structure | HPLC time (min.) | MS (M+) |
|---|---|---|---|
| 55 | 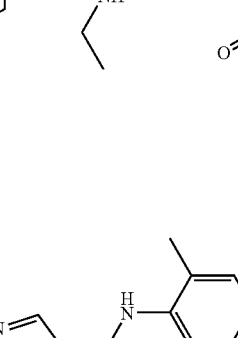 | 3.23 | 445.2 |
| 56 | 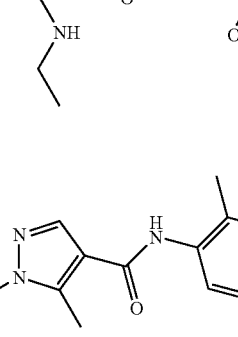 | 2.99 | 432.1 |
| 57 | 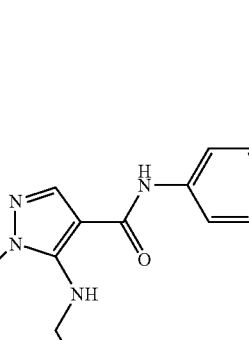 | 2.82 | 417.1 |
| 58 | 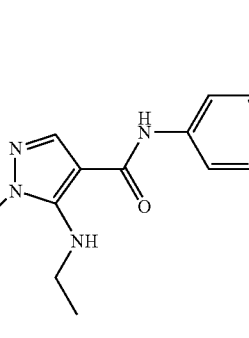 | 3.46 | 373.2 |
| 59 | 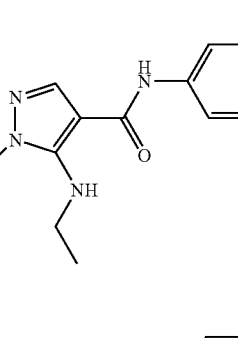 | 2.86 | 362.1 |

TABLE 3-continued

| Ex. No. | Structure | HPLC time (min.) | MS (M+) |
|---|---|---|---|
| 60 | 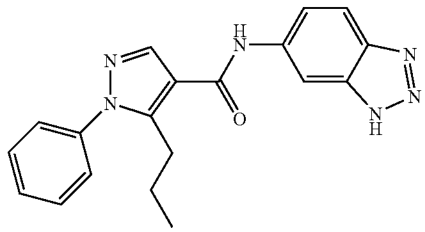 | 3.04 | 347.1 |
| 61 | 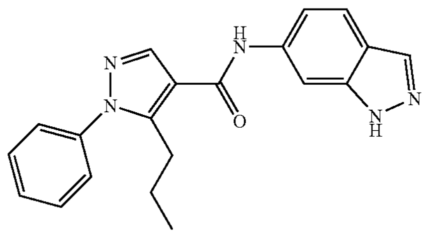 | 3.14 | 346.1 |
| 62 | 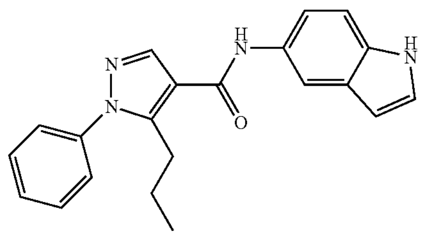 | 3.12 | 345.1 |
| 63 | 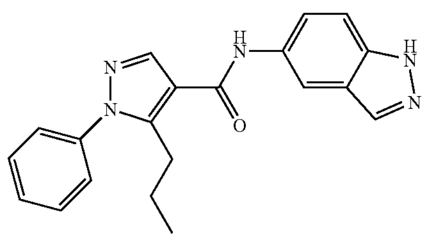 | 3.05 | 346.1 |
| 64 | 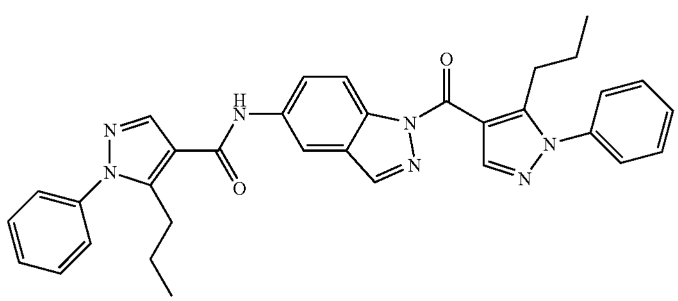 | 4.22 | 558.3 |
| 65 | 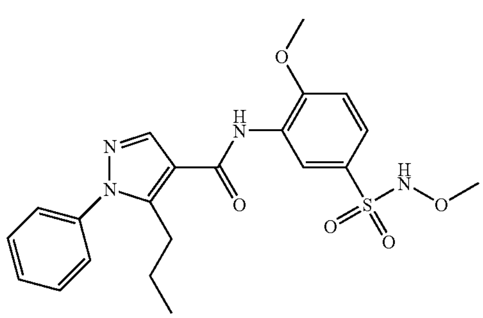 | 3.13 | 445.2 |

TABLE 3-continued

| Ex. No. | Structure | HPLC time (min.) | MS (M+) |
|---|---|---|---|
| 66 | 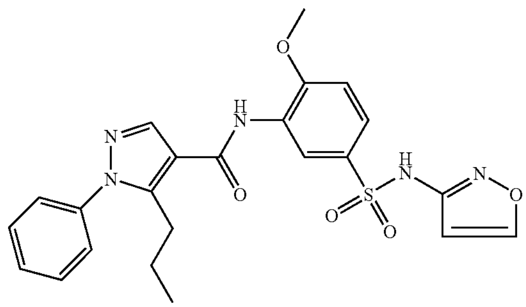 | 3.11 | 482.2 |
| 67 | 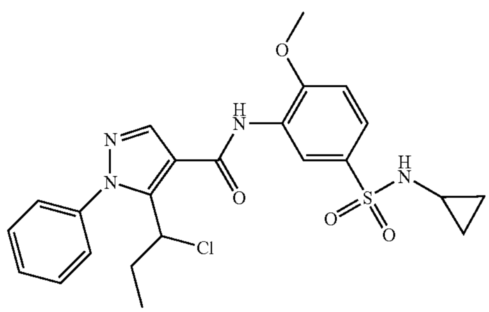 | 3.35 | 489.2 |
| 68 | 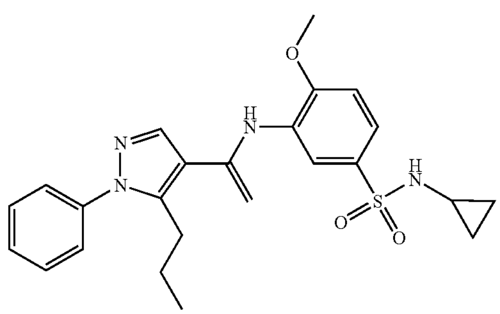 | 3.25 | 455.2 |
| 69 | 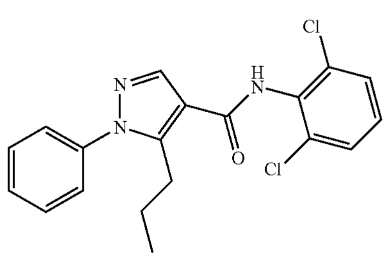 | 3.28 | 374.2 |
| 70 | 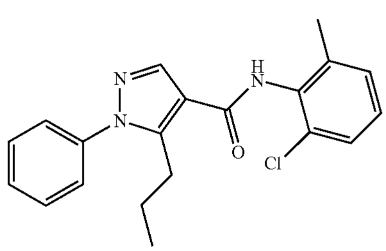 | 3.30 | 354.2 |

TABLE 3-continued

| Ex. No. | Structure | HPLC time (min.) | MS (M+) |
|---|---|---|---|
| 71 | 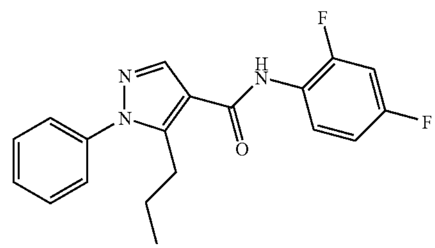 | 3.36 | 342.2 |
| 72 | 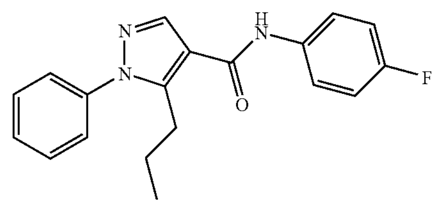 | 3.42 | 324.2 |
| 73 | 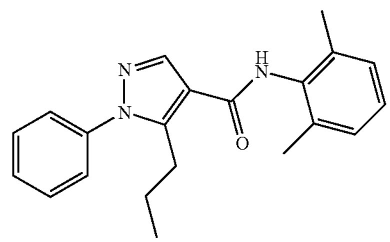 | 3.31 | 334.3 |
| 74 | 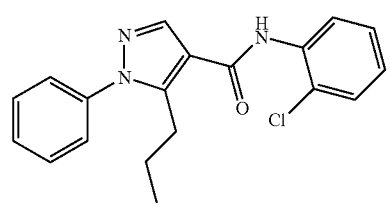 | 3.46 | 340.1 |
| 75 | 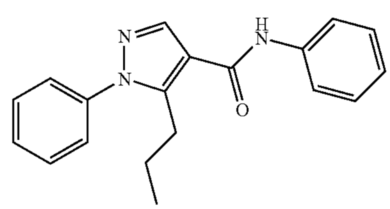 | 3.35 | 306.2 |
| 76 | 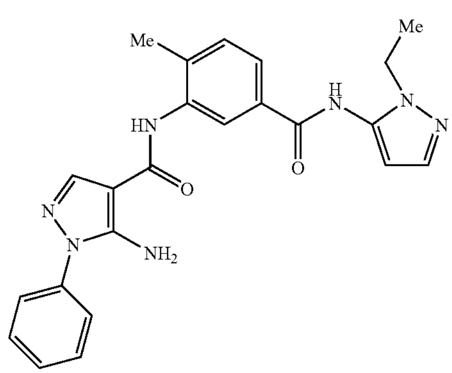 | 430.12 | 1.37[a] |

TABLE 3-continued

| Ex. No. | Structure | HPLC time (min.) | MS (M+) |
|---|---|---|---|
| 77 | 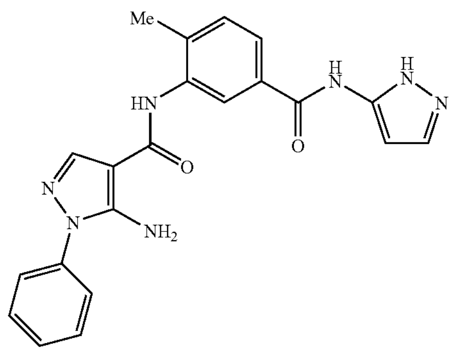 | 402.10 | 1.31[a] |
| 78 | 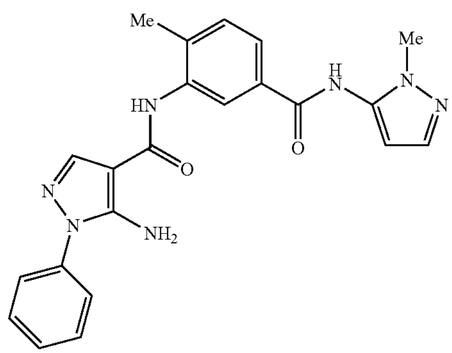 | 416.18 | 1.32[a] |
| 79 | 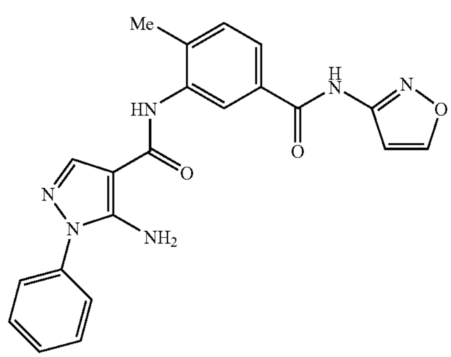 | 403.06 | 1.38[a] |
| 80 | 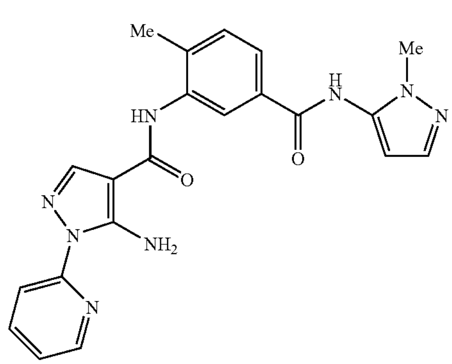 | 417.08 | 1.44[a] |

TABLE 3-continued

| Ex. No. | Structure | HPLC time (min.) | MS (M+) |
|---|---|---|---|
| 81 | 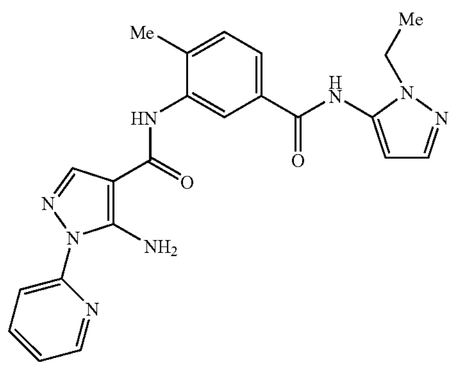 | 431.09 | 1.48[a] |
| 82 | 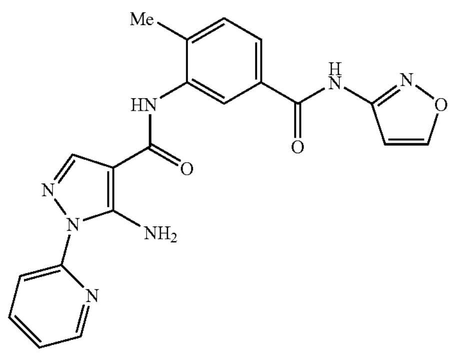 | 404.36 | 1.77[a] |
| 83 | 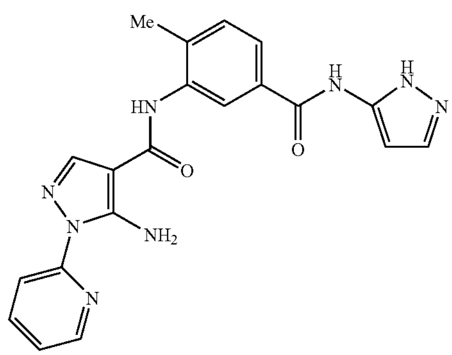 | 403.10 | 1.43[a] |
| 84 | 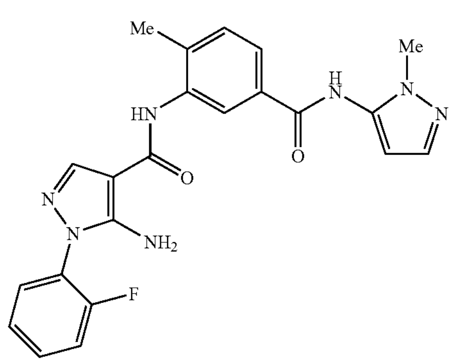 | 434.16 | 1.28[a] |

TABLE 3-continued

| Ex. No. | Structure | HPLC time (min.) | MS (M+) |
|---|---|---|---|
| 85 | 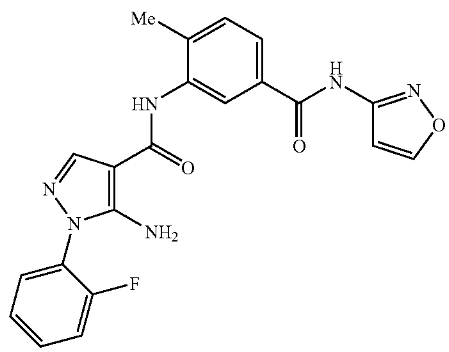 | 421.18 | 1.35[a] |
| 86 | 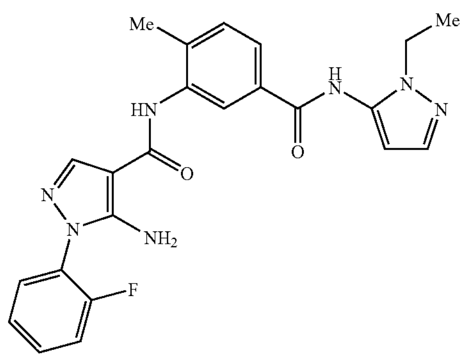 | 448.11 | 1.34[a] |
| 87 | 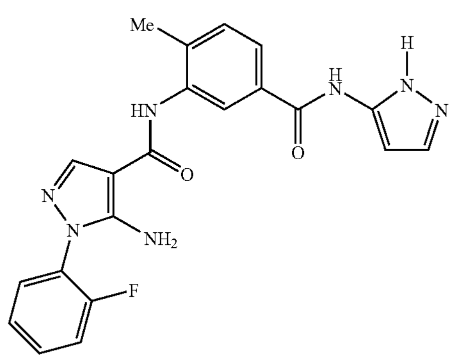 | 420.18 | 1.26[a] |
| 88 | 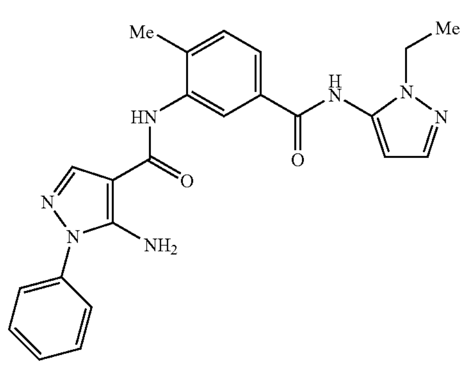 | 430.12 | 1.37[a] |

TABLE 3-continued

| Ex. No. | Structure | HPLC time (min.) | MS (M+) |
|---|---|---|---|
| 89 | 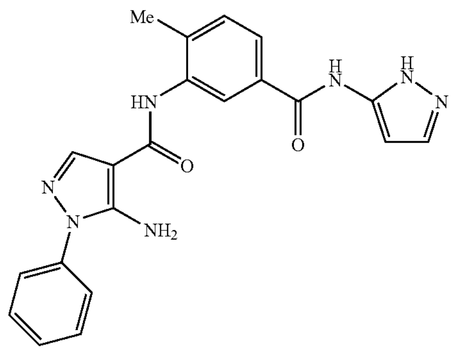 | 402.10 | 1.31[a] |
| 90 | 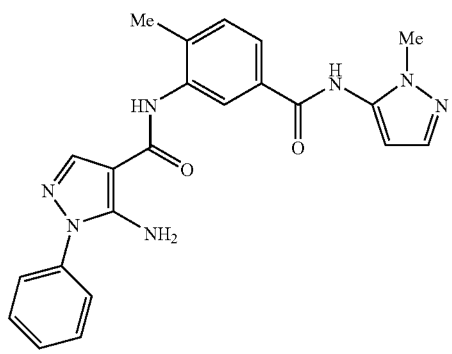 | 416.18 | 1.32[a] |
| 91 | 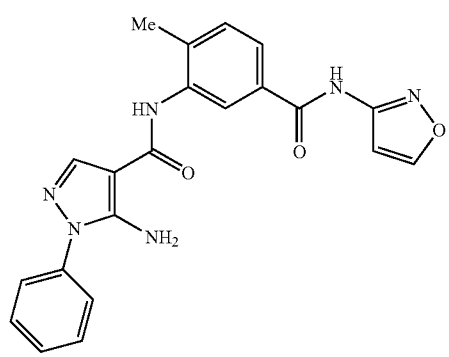 | 403.06 | 1.38[a] |
| 92 | 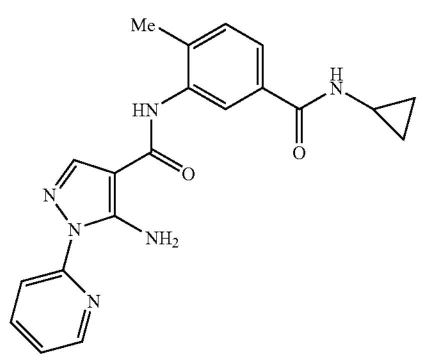 | 377.10 | 1.47[a] |

TABLE 3-continued

| Ex. No. | Structure | HPLC time (min.) | MS (M+) |
|---|---|---|---|
| 93 | 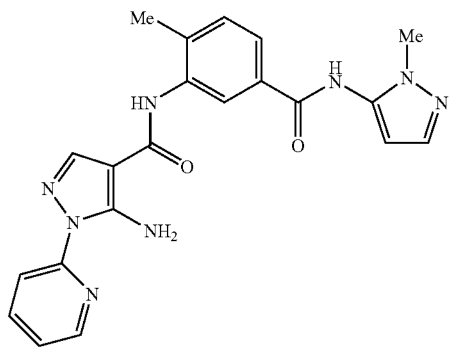 | 417.08 | 1.44[a] |
| 94 | 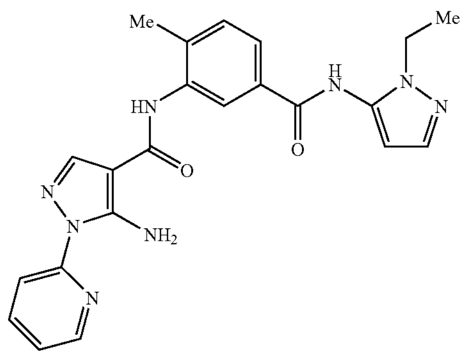 | 431.09 | 1.48[a] |
| 95 | 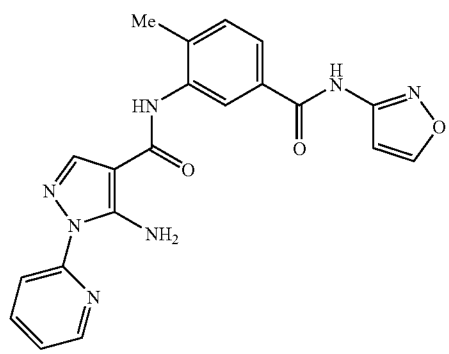 | 404.36 | 1.77[a] |
| 96 | 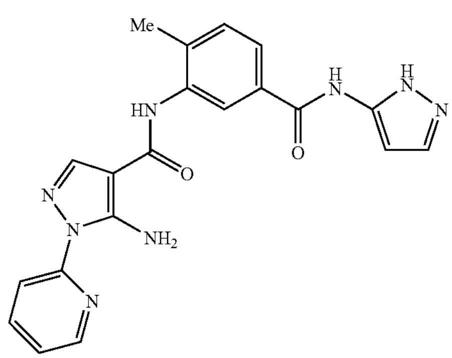 | 403.10 | 1.43[a] |

TABLE 3-continued
| Ex. No. | Structure | HPLC time (min.) | MS (M+) |
|---|---|---|---|
| 97 | 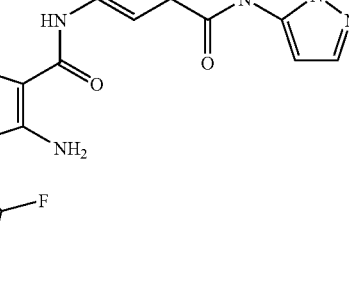 | 434.16 | 1.28[a] |
| 98 | 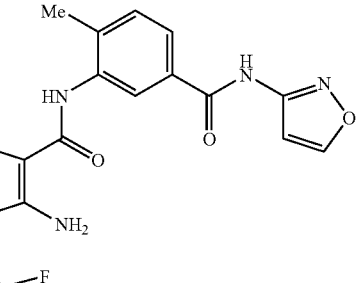 | 421.18 | 1.35[a] |
| 99 | 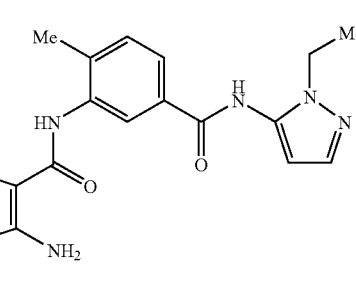 | 448.11 | 1.34[a] |
| 100 | 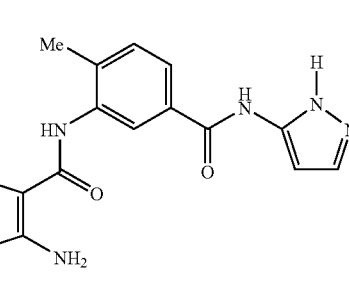 | 420.18 | 1.26[a] |

TABLE 3-continued

| Ex. No. | Structure | HPLC time (min.) | MS (M+) |
|---|---|---|---|
| 101 | 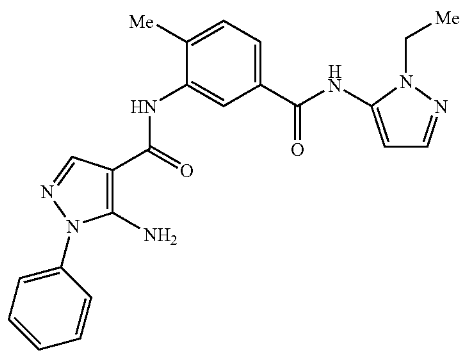 | 430.12 | 1.37[a] |
| 102 | 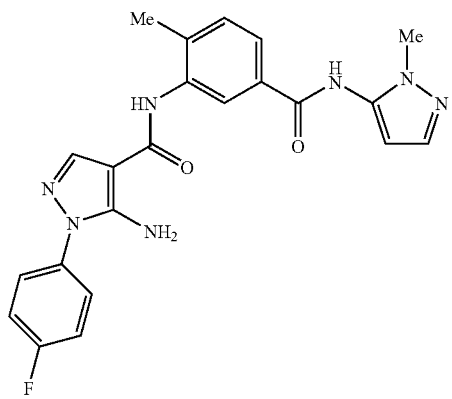 | 434.16 | 1.37[a] |
| 103 | 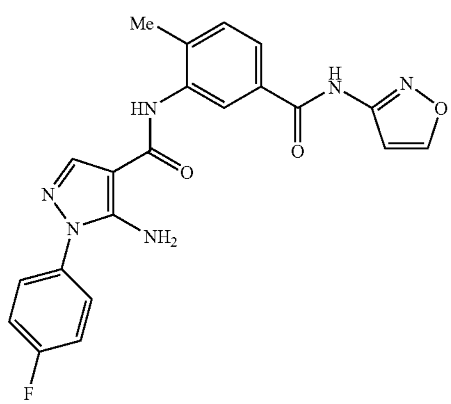 | 421.18 | 1.43[a] |
| 104 | 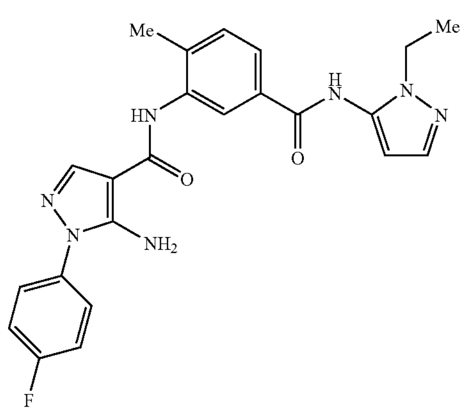 | 448.18 | 1.41[a] |

TABLE 3-continued

| Ex. No. | Structure | HPLC time (min.) | MS (M+) |
|---|---|---|---|
| 105 | 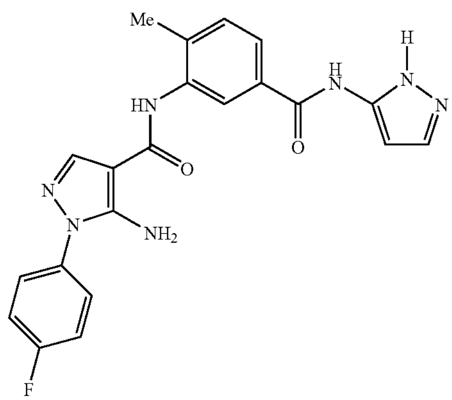 | 420.14 | 1.34[a] |
| 106 | 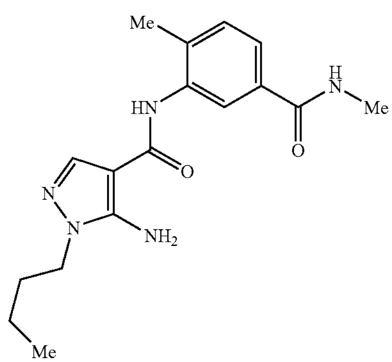 | 330.22 | 1.25[a] |
| 107 | 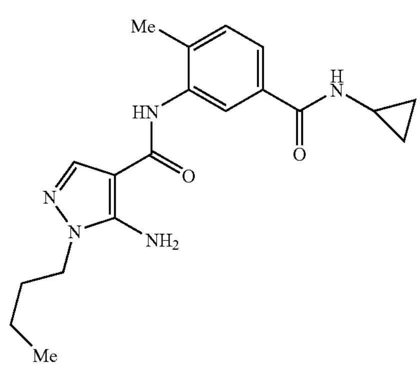 | 356.25 | 1.36[a] |
| 108 | 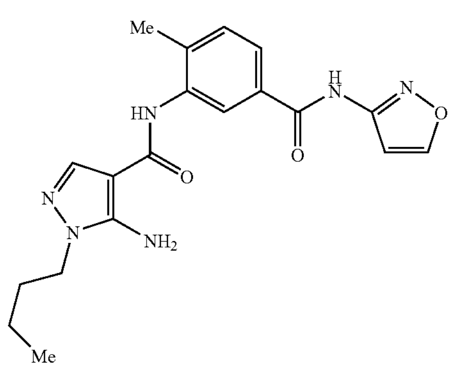 | 383.19 | 1.40[a] |

TABLE 3-continued

| Ex. No. | Structure | HPLC time (min.) | MS (M+) |
|---|---|---|---|
| 109 | 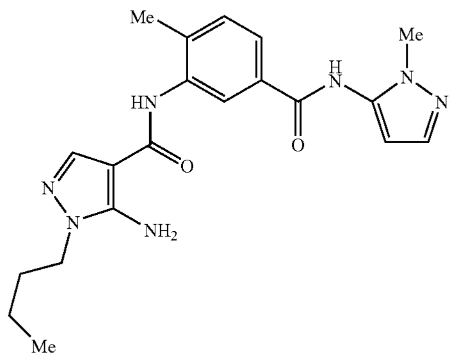 | 396.24 | 1.34[a] |
| 110 | 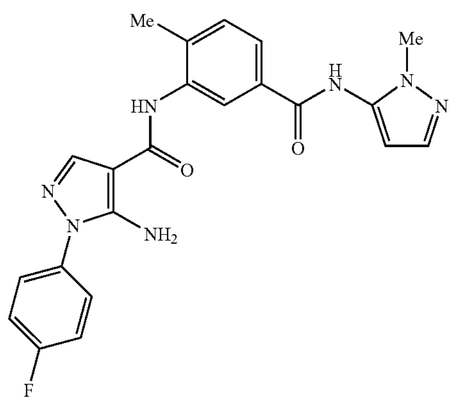 | 434.16 | 1.37[a] |
| 111 | 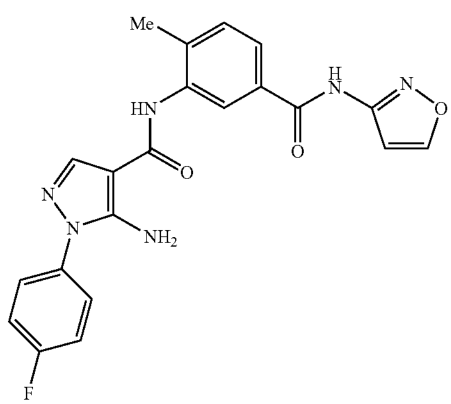 | 421.18 | 1.43[a] |
| 112 | 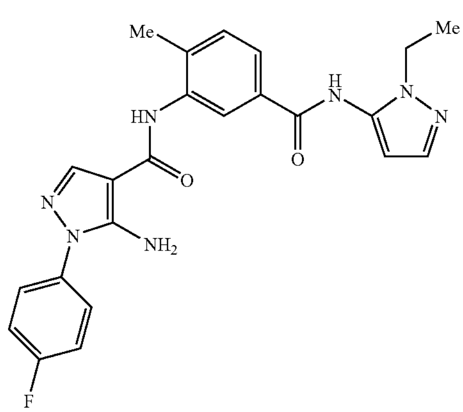 | 448.18 | 1.41[a] |

TABLE 3-continued

| Ex. No. | Structure | HPLC time (min.) | MS (M+) |
|---|---|---|---|
| 113 | 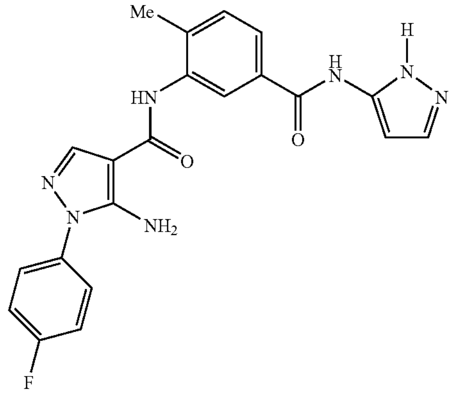 | 420.14 | 1.34[a] |
| 114 | 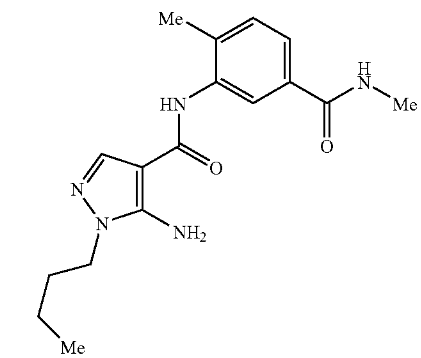 | 330.22 | 1.25[a] |
| 115 | 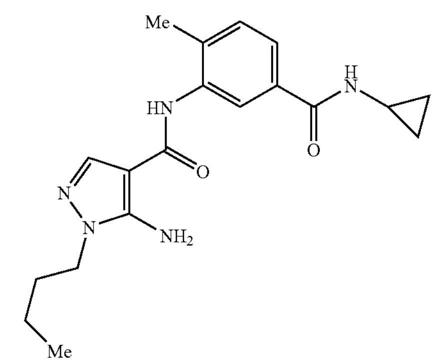 | 356.25 | 1.36[a] |
| 116 | 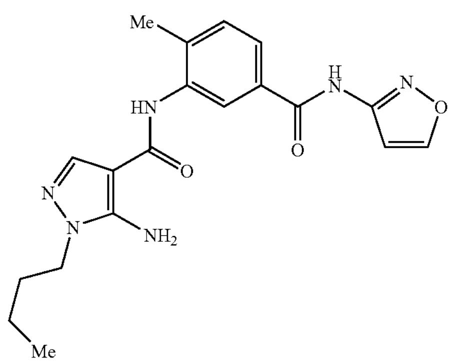 | 383.19 | 1.40[a] |

It is noted that Examples 117-200 below are prophetic examples.

Example 117

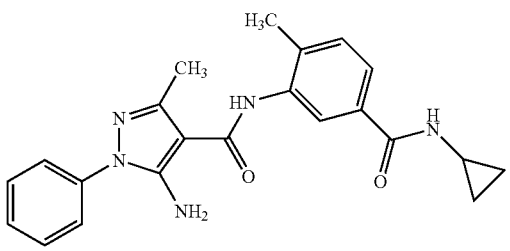

Step A:

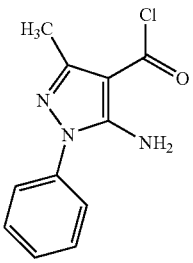

A suspension of 5-amino-3-methyl-1-phenyl-pyrazole-4-carboxylic acid in thionyl chloride is stirred at rt for 1.75 h. The mixture is concentrated under reduced pressure and is dried in vacuo to obtain the above acid chloride.

Step B:

Compound from step A is added to a solution of 3-cyclopropylcarboxamido-6-methylaniline in DCM and pyridine at reduced temperature. The cooling bath is removed after addition and the solution is stirred at rt for 15 min. The reaction mixture is concentrated and the residue diluted with 0.5 N aq. HCl solution. The precipitate is sonicated for several min and filtered. The solid is washed with 0.5 N aq. HCl solution, satd. aq. HaHCO$_3$ solution, water and is dried to obtain Example 117.

Example 118

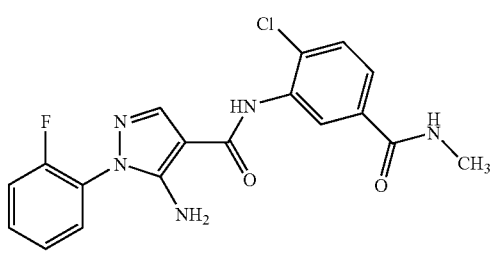

Step A:

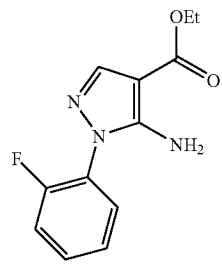

Ethyl(ethoxymethylene)-cyanoacetate is was added in portions to a suspension of 2-fluorophenylhydrazine hydrochloride and triethyl amine in absolute EtOH. The mixture is stirred for 50 min, diluted with water and extracted with EtOAc. The organic extracts are combined, washed with water, brine, dried (Na2SO4), filtered, and concentrated under reduced pressure an in vacuo to obtain the above compound.

Step B:

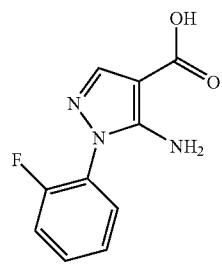

A solution of compound from step A in THF: MeOH and 2.5 N aq. NaOH solution is heated to 60° C. for 8 h. The mixture is concentrated under reduced pressure and acidified with 6 N aq. HCl solution at 0° C. The precipitated solid is collected by filtration, washed with water and DCM, and is dried to obtain the above acid.

Step C:

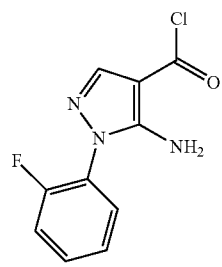

A solution of carboxylic acid from step B in thionyl chloride is stirred at rt for 2 h. The mixture is concentrated under reduced pressure and in vacuo to obtain the above acid chloride.

Step D:

Compound from Step C is added to a solution of 3-methylcarboxamido-6-chloro-aniline in DCM and pyridine at 0° C. The cooling bath is removed after addition and the solution is stirred at rt for 45 min. The reaction mixture is concentrated and the residue is diluted with 0.5 N aq. HCl solution (8 mL). The precipitated solid is sonicated for several min and filtered. The solid is washed with 0.5 N aq. HCl solution, satd. aq. NaHCO$_3$ solution, water and is dried in vacuo to obtain the above Example 118.

Example 119

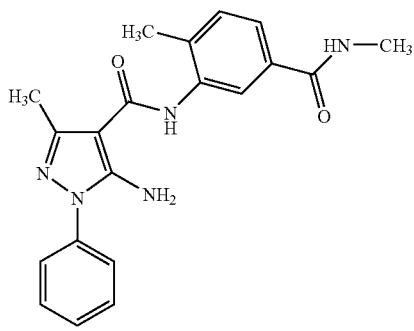

Step A:

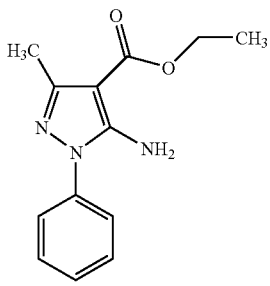

Phenyl hydrazine, ethyl (ethoxymethylene)-cyanoacetate, and absolute EtOH are refluxed 1 hr. The reaction volume is reduced by one-half and cooled in ice, and the desired product is collected by filtration. The filtrate volume is further reduced, cooled, and then filtered to collect the above compound.

Step B:

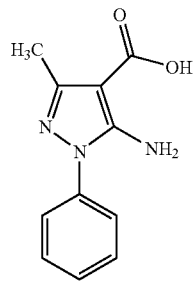

Compound from step A, THF, MeOH and 3N NaOH are combined and refluxed 4 hrs. Most of solvent is removed by evaporation and the remainder is neutralized with 1 N HCl. The solid product is collected by filtration, washed, and is dried to give the above compound.

Step C: Example 119

Compound from Step B, thionyl chloride, THF and DMF are refluxed briefly. The cloudy reaction solution is filtered through a medium glass frit, evaporated, and the residue is triturated with 9:1 hexanes:diethyl ether to yield a product. This is redissolved into THF and was slowly is added to a second reaction solution containing 3-amino-4-methyl methylbenzamide and pyridine in THF at 0 deg C. The reaction is allowed to stir overnight and reach rt. Reaction is evaporated and the product is washed with 1 N HCl, 1 N NaOH, and is dried to yield the above Example 119.

Example 120

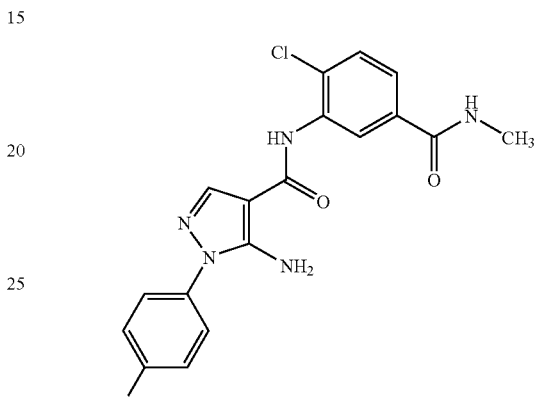

Step A:

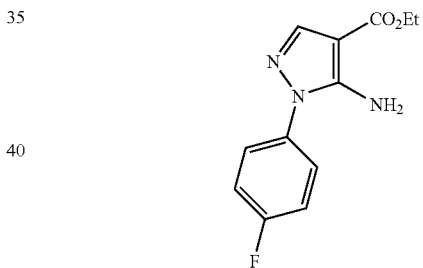

Ethyl(ethoxymethylene)cyanoacetate and 4-fluorophenylhydrazine hydrochloride are mixed in absolute EtOH at RT and triethylamine is introduced via syringe dropwise. The mixture is stirred overnight, diluted with ether and filtered. The filtrate is diluted with EtOAc and is washed with water, brine, dried over Na$_2$SO$_4$, filtered, and is concentrated under reduced pressure to obtain the above compound.

Step B:

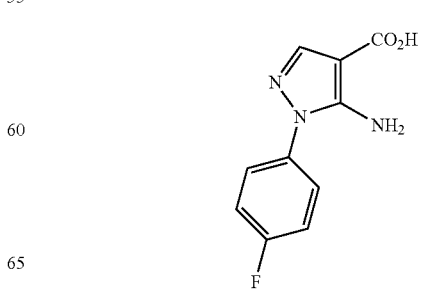

A solution of compound from Step A in absolute EtOH and 3 N aq. NaOH solution is refluxed for 2 h. The mixture is concentrated under reduced pressure and is taken up in water and is washed with DCM. The aqueous layer is acidified with 6 N aq. HCl solution at 0° C., and the precipitate is collected by filtration, is washed with water, and is dried to obtain the above acid.

Step C: Example 120

To a slurry of carboxylic acid from step B in DCM is added thionyl chloride. After 10 min, DMF is added, then the solution is stirred at RT. The mixture is concentrated under reduced pressure to obtain a product. The product is slurred in DCM and cooled to 0° C. whereupon 3-methylcarboxamido-6-chloroaniline is added and is followed by a dropwise addition of a solution of pyridine in DCM over 15 min. After the addition is complete, the cooling bath is removed and the solution is stirred at rt for 30 min. The reaction mixture is concentrated and the residue is treated with water and 1N aq. HCl. The resulting slurry is sonicated for several minutes, filtered, and is washed with 1 N aq. HCl solution, water and is dried in vacuo. The product is triturated with hot EtOAc, hot ether, then washed with acetonitrile and is decolorized in MeOH using charcoal. The filtrate is concentrated and the resulting solid is recrystallized from MeOH/acetonitrile to afford the above Example 120.

Examples 121-130

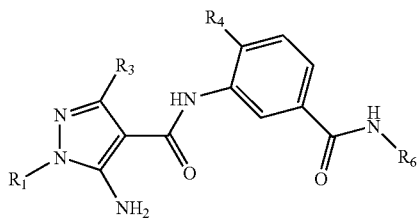

Examples 121 to 130, having the above formula wherein the variables $R_1$, $R_3$, $R_4$ and $R_6$ have the values shown in Table 4 are prepared following the procedures described in the preparation of the foregoing Examples 117 through 120.

TABLE 4

| Ex.# | $R_1$ | $R_6$ | $R_3$ | $R_4$ |
|---|---|---|---|---|
| 121 | 2-pyridyl | —CH₃ | —CH₃ | —CH₃ |
| 122 | 2-pyridyl | cyclopropyl | —CH₃ | —CH₃ |
| 123 | 2-fluorophenyl | cyclopropyl | —CH₃ | —CH₃ |

TABLE 4-continued

| Ex.# | $R_1$ | $R_6$ | $R_3$ | $R_4$ |
|---|---|---|---|---|
| 124 | 4-fluorophenyl | cyclopropyl | —CH₃ | —CH₃ |
| 125 | phenyl | —CH₃ | —CH₃ | —CH₃ |
| 126 | 2-pyridyl | —CH₃ | —H | —Cl |
| 127 | 2-pyridyl | cyclopropyl | —H | —Cl |
| 128 | 2-fluorophenyl | cyclopropyl | —H | —Cl |
| 129 | 4-fluorophenyl | cyclopropyl | —H | —Cl |
| 130 | phenyl | —CH₃ | —H | —Cl |

Example 131

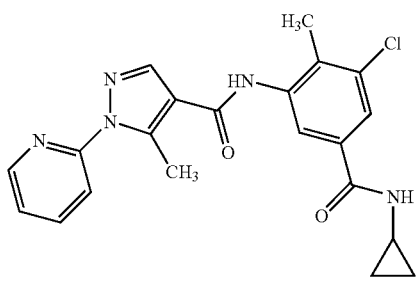

Step A:

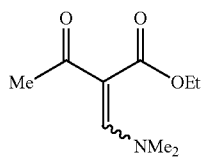
(131A)

To ethyl acetoacetate is added p-TsOH and DMF-DMA. The solution is heated at 100° C. for 2.5 hr, then cooled to RT. A distillation apparatus is attached and the product is purified by fractional distillation under vacuum to give (131A).

Step B:

(131B)

To a solution of (131A) in EtOH is added pyridin-2-yl-hydrazine. The solution is heated to 65° C. for 3 h, then aq NaOH is added and the reaction is allowed to cool to RT overnight. The EtOH is evaporated and the resulting aqueous solution is acidified to approximately pH 3. The resulting precipitate is collected by filtration and allowed to air dry, affording (131B).

Step C:

To a solution of (131B) in NMP is added BOP, DIPEA and 3-amino-5-chloro-N-cyclopropyl-4-methyl-benzamide hydrochloride. The solution is heated to 50° C. and allowed to stir overnight. The reaction is heated to 80° C. for an additional 4 hr. The solution is cooled to RT and water is added. The product is extracted with EtOAc to afford a crude product that can be further purified.

Examples 132-186

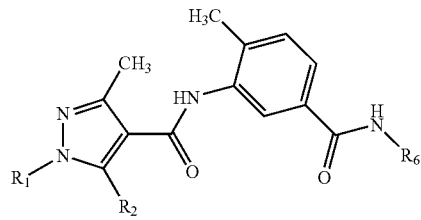
(Core A)

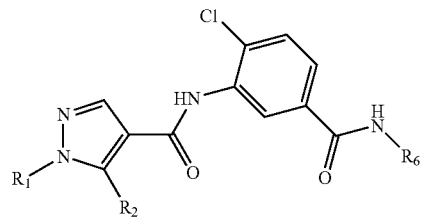
(Core B)

Examples 132-186, having the above formula of Core A or Core B, wherein the variables $R_1$, $R_2$ and $R_6$ have the values shown in Table 5 can be prepared following the procedures described in the preparation of Examples 117-120 and 131.

TABLE 5

| Ex. No. | Core | $R_1$ | $R_2$ | $R_6$ |
|---|---|---|---|---|
| 132 | A | 3-fluorophenyl | —CH₃ | cyclopropyl |
| 133 | A | 2-fluorophenyl | —CH₃ | cyclopropyl |
| 134 | A | 6-ethoxypyridazin-3-yl | —CH₃ | cyclopropyl |
| 135 | A | 3,5-dichloropyridin-4-yl | —CH₃ | cyclopropyl |

TABLE 5-continued
| Ex. No. | Core | R₁ | R₂ | R₆ |
|---|---|---|---|---|
| 136 | A | 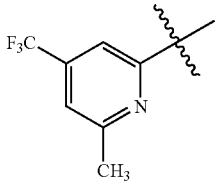 | —CH₃ | 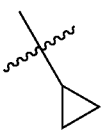 |
| 137 | A | 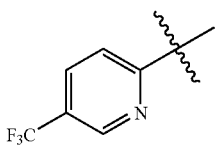 | —CH₃ | 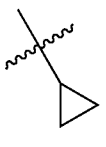 |
| 138 | A | 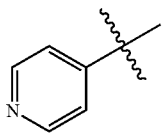 | —CH₃ | 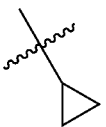 |
| 139 | A | 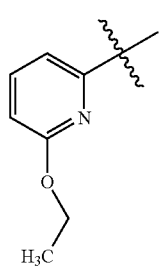 | —CH₃ | 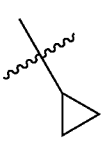 |
| 140 | A | 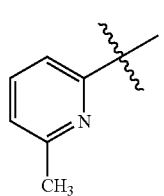 | —CH₃ | 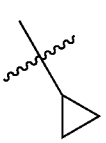 |
| 141 | A | 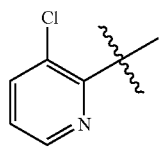 | —CH₃ | 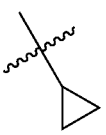 |
| 142 | A | 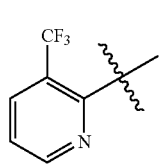 | —CH₃ | 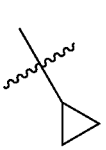 |
| 143 | A | 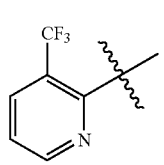 | —CH₃ | 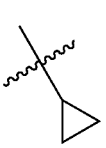 |

TABLE 5-continued

| Ex. No. | Core | R₁ | R₂ | R₆ |
|---|---|---|---|---|
| 144 | A | 2-ethylphenyl | —CH₃ | cyclopropyl |
| 145 | A | 4-methylphenyl | —CH₃ | cyclopropyl |
| 146 | A | 3-methylphenyl | —CH₃ | cyclopropyl |
| 147 | A | 2-methylphenyl | —CH₃ | cyclopropyl |
| 148 | A | 3-(trifluoromethyl)pyridin-2-yl | —NH₂ | cyclopropyl |
| 149 | A | phenyl | n-propyl | —CH₃ |
| 150 | A | phenyl | n-propyl | cyclopropyl |
| 151 | A | pyridin-3-yl | —CH₃ | cyclopropyl |
| 152 | A | 3-(methylsulfonyl)phenyl | —CH₃ | cyclopropyl |

TABLE 5-continued
| Ex. No. | Core | R₁ | R₂ | R₆ |
|---|---|---|---|---|
| 153 | A | 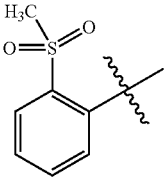 | —CH₃ | 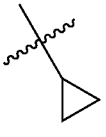 |
| 154 | A | 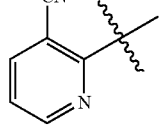 | —CH₃ | 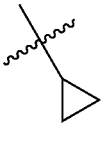 |
| 155 | A | 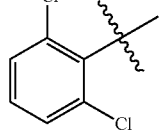 | —CH₃ | 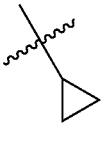 |
| 156 | A | 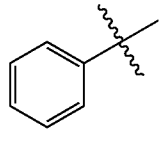 | n-propyl | n-propyl |
| 157 | A | 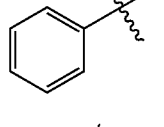 | n-propyl | Et |
| 158 | A | 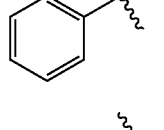 | n-propyl | —CH₂—CH(CH₃)₂ |
| 159 | B | 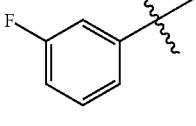 | —CH₃ | 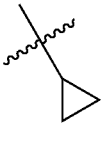 |
| 160 | B | 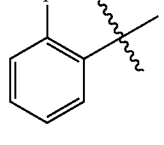 | —CH₃ | 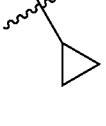 |
| 161 | B | 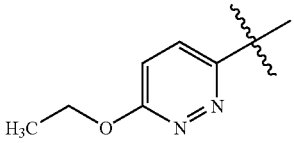 | —CH₃ | 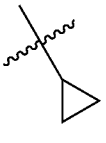 |
| 162 | B | 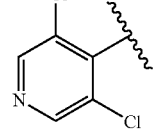 | —CH₃ | 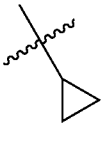 |

TABLE 5-continued

| Ex. No. | Core | R₁ | R₂ | R₆ |
|---|---|---|---|---|
| 163 | B | 4-CF₃-6-methyl-pyridin-2-yl | —CH₃ | cyclopropyl |
| 164 | B | 5-CF₃-pyridin-2-yl | —CH₃ | cyclopropyl |
| 165 | B | pyridin-4-yl | —CH₃ | cyclopropyl |
| 166 | B | 6-ethoxy-pyridin-2-yl | —CH₃ | cyclopropyl |
| 167 | B | 6-methyl-pyridin-2-yl | —CH₃ | cyclopropyl |
| 168 | B | 3-chloro-pyridin-2-yl | —CH₃ | cyclopropyl |
| 169 | B | 3-CF₃-pyridin-2-yl | —CH₃ | cyclopropyl |
| 170 | B | 3-CF₃-pyridin-2-yl | —CH₃ | cyclopropyl |

TABLE 5-continued

| Ex. No. | Core | R₁ | R₂ | R₆ |
|---------|------|----|----|----|
| 171 | B | 3-ethylphenyl | —CH₃ | cyclopropyl |
| 172 | B | 4-methylphenyl | —CH₃ | cyclopropyl |
| 173 | B | 3-methylphenyl | —CH₃ | cyclopropyl |
| 174 | B | 2-methylphenyl | —CH₃ | cyclopropyl |
| 175 | B | 3-(trifluoromethyl)pyridin-2-yl | —NH₂ | cyclopropyl |
| 176 | B | phenyl | n-propyl | —CH₃ |
| 177 | B | phenyl | n-propyl | cyclopropyl |
| 178 | B | pyridin-3-yl | —CH₃ | cyclopropyl |
| 179 | B | 3-(methylsulfonyl)phenyl | —CH₃ | cyclopropyl |
| 180 | B | 2-(methylsulfonyl)phenyl | —CH₃ | cyclopropyl |

TABLE 5-continued
| Ex. No. | Core | R₁ | R₂ | R₆ |
|---|---|---|---|---|
| 181 | B | 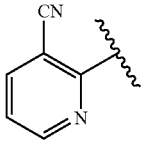 | —CH₃ | 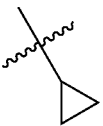 |
| 182 | B | 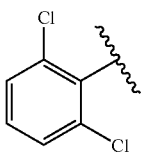 | —CH₃ |  |
| 183 | B | 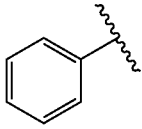 | n-propyl | n-propyl |
| 184 | B | 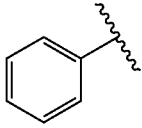 | n-propyl | Et |
| 185 | B | 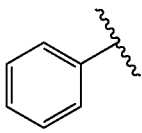 | n-propyl | —CH₂—CH(CH₃)₂ |
| 186 | B | 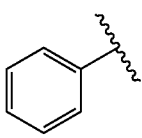 | n-propyl | Iso-Pr |

Examples 187-190

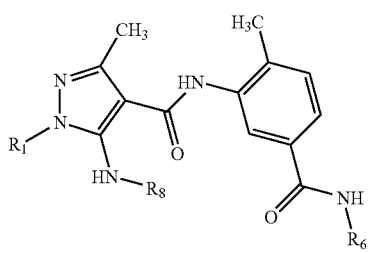

Examples 187-190, having the above formula wherein the variables $R_1$, $R_6$ and $R_8$ have the values shown in Table 6, can be prepared following the procedures described in the previous examples and schemes.

TABLE 6

| Ex. No. | $R_1$ | $R_8$ | $R_6$ |
|---|---|---|---|
| 187 | 2-methylphenyl | Et | Et |
| 188 | 2-pyridyl | Et | Et |
| 189 | phenyl | Et | Et |
| 190 | 2-methylphenyl | Et | cyclopropyl |

Example 191

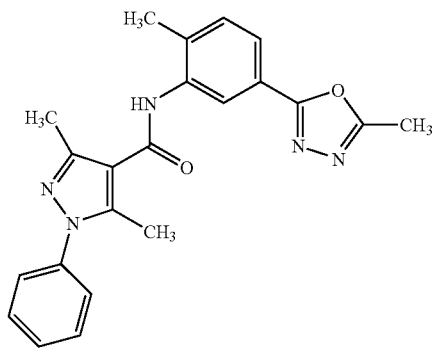

Step A:

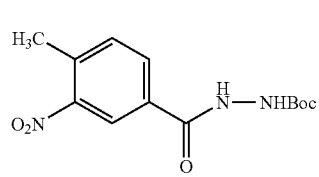
(191A)

To a rt solution of tert-butyl carbazate and triethylamine in DCE is added a solution of 4-methyl-3-nitrobenzoyl chloride in DCE over 30 minutes. After the addition is complete the resulting cloudy mixture is stirred at rt for 2 h then the mixture is successively washed with 10% aqueous citric acid and brine, then dried over anhydrous sodium sulfate. The solution is diluted with EtOAc, is filtered, and is concentrated in vacuo. The mixture is diluted with hexanes and sonicated for a few minutes, and the resulting precipitated solid is collected by vacuum filtration and is dried in vacuo to afford the above compound (191A).

Step B:

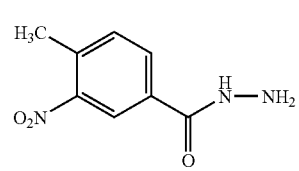
(191B)

Compound 191A from step A is added in portions to trifluoroacetic acid at 0° C. and the mixture is stirred at this temperature for 30 min and at rt for an additional 30 minutes. The mixture is then concentrated in vacuo and the resulting white solid is partitioned between 2N aq sodium carbonate and EtOAc. The layers are separated and the aqueous portion is extracted with additional EtOAc, and the combined extracts are washed with brine, dried over anhydrous sodium sulfate, filtered, and concentrated in vacuo to yield the above compound 191B.

Step C:

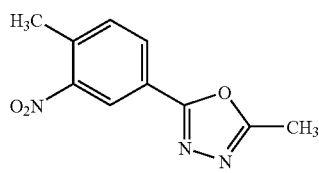
(191C)

A suspension of compound 191B in triethyl orthoacetate is heated to 100° C. giving a clear solution. After heating at this temperature for 2 h, the mixture is heated to 130° C. for an additional hour then cooled to rt and heterogeneously concentrated in vacuo. The resulting residue is dissolved in EtOAc and washed with water and brine and is then dried over anhydrous sodium sulfate, is filtered, and concentrated in vacuo to afford compound 191C.

Step D:

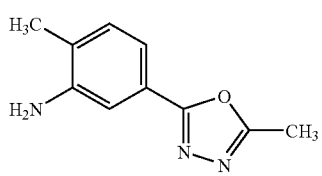

(191D)

To a suspension of compound 191C in EtOH is added 5% Pd/C and the mixture is allowed to stir under an atmosphere of hydrogen at rt for 2 h. The mixture is filtered through Celite and the resulting clear filtrate is concentrated in vacuo and the residue is triturated with methanol. Filtration and drying of the collected solid affords compound 191D.

Step E: Example 191

A mixture of 3,5-diMethyl-1-phenyl-1H-pyrazole-4-carboxylic acid, 1-[3-(dimethylamino)propyl]-3-ethylcarbodiimide hydrochloride and 1-hydroxybenzotriazole in anhydrous DMF is reacted at rt for 1.5 h. At this time, aniline (191D) is added as solid and then is added DIPEA. The mixture is then heated at 60° C. for 16 h then the solution is diluted with water and allowed to cool to RT. The resulting solid is collected by vacuum filtration and is dried in vacuo to afford Example 191.

Examples 192-97

Examples 192-97, having the above formula wherein the variables $R_1$ and $R_2$ have the values shown in Table 7, can be prepared following the procedure described in the preparation of Example 191.

TABLE 7

| Ex. No. | $R_1$ | $R_2$ |
|---|---|---|
| 192 | 2-fluorophenyl | $CH_3$ |
| 193 | 3-fluorophenyl | $CH_3$ |
| 194 | 4-fluorophenyl | $CH_3$ |
| 195 | 2,5-difluorophenyl | $CH_3$ |
| 196 | 2-pyridyl | $CH_3$ |
| 197 | phenyl | $HN-CH_3$ |

Examples 198-200

Compounds having the formula below for Examples 198-200, can be prepared following the procedures described in the previous examples and schemes, wherein unspecified variables of $R_1$, $R_2$, and $R_6$ can be selected from those shown above in Tables 1-7 above.

| Ex. | Formula |
|---|---|
| 198 | (pyrazole-carboxamide-oxadiazole structure) |
| 199 | (pyrazole-carboxamide-chlorophenyl-carboxamide $R_6$ structure) |

| Ex. | Formula |
|---|---|
| 200 | 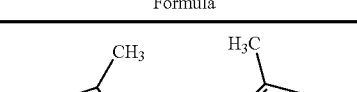 |

We claim:

1. A compound having the formula (I),

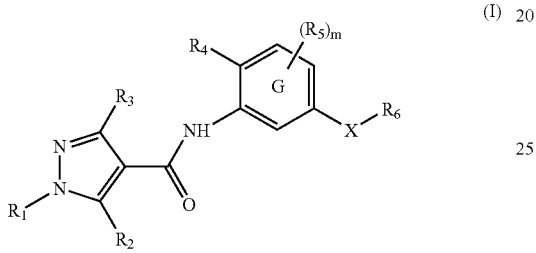

wherein G is phenyl;

$R_1$ is hydrogen, alkyl, substituted alkyl, aryl, substituted aryl, heteroaryl, substituted heteroaryl, cycloalkyl, substituted cycloalkyl, heterocyclo or substituted heterocyclo, or $C(=O)R_{18}$;

$R_2$ is hydrogen, hydroxyl(alkyl), alkoxy(alkyl), halogen, haloalkyl, cyanoalkyl, alkoxy, substituted alkoxy, or $R_{2a}$, wherein $R_{2a}$ is $C_{1-6}$alkyl, amino, alkylamino, substituted alkylamino, cycloamino, substituted cycloamino, or $C_{1-6}$alkyl substituted with one to two of amino, alkylamino, substituted alkylamino, cycloamino, and/or substituted cycloamino;

$R_3$ is hydrogen, haloalkyl, haloalkoxy, halogen, cyano, nitro, $C_{1-4}$alkyl, substituted $C_{1-4}$alkyl, $NR_{11}R_{12}$, or $OR_{11}$;

$R_4$ is hydrogen, $C_{1-4}$alkyl, substituted $C_{1-4}$alkyl, halogen, haloalkyl, haloalkoxy, cyano, nitro, or $OR_{13}$;

$R_5$ is at each occurrence independently selected from haloalkyl, haloalkoxy, cyano, nitro, alkyl or substituted alkyl, alkenyl or substituted alkenyl, alkynyl or substituted alkynyl, cycloalkyl or substituted cycloalkyl, heterocycle or substituted heterocycle, aryl or substituted aryl, heteroaryl or substituted heteroaryl, $OR_{13}$, $SR_{13}$, $S(=O)R_{14}$, $S(=O)_2R_{14}$, $P(=O)_2R_{14}$, $S(=O)_2OR_{15}$, $P(=O)_2OR_{14}$, $NR_{13}R_{14}$, $NR_{13}S(=O)_2R_{15}$, $NR_{13}P(=O)_2R_{14}$, $S(=O)_2NR_{13}R_{14}$, $P(=O)_2NR_{13}R_{14}$, $C(=O)OR_{13}$, $C(=O)R_{13}$, $C(=O)NR_{13}R_{14}$, $OC(=O)R_{13}$, $OC(=O)NR_{13}R_{14}$, $NR_{13}C(=O)OR_{14}$, $NR_{16}C(=O)NR_{13}R_{14}$, $NR_{16}S(=O)_2NR_{13}R_{14}$, $NR_{16}P(=O)_2NR_{13}R_{14}$, $NR_{13}C(=O)R_{14}$, or $NR_{13}P(=O)_2R_{14}$;

X is —(C=O)NH—;

$R_6$ is hydrogen, alkyl, alkoxy or substituted alkoxy, phenoxy or substituted phenoxy, cycloalkyl or substituted cycloalkyl, heterocycle or substituted heterocycle, aryl or substituted aryl, heteroaryl or substituted heteroaryl; or where X is absent, $R_6$ can also be selected from halogen, cyano, trifluoromethyl, alkyl, amino, and/or alkylamino; or alternatively, $R_6$ is joined together with a group $R_5$ on an adjacent carbon atom to form an optionally-substituted, fused five to six membered heterocyclic or carbocyclic ring;

$R_{11}$, $R_{12}$, $R_{13}$, $R_{14}$, $R_{15}$, $R_{16}$ and $R_{17}$ are independently at each occurrence selected from hydrogen, alkyl, substituted alkyl, cycloalkyl or substituted cycloalkyl, heterocycle or substituted heterocycle, aryl or substituted aryl, and heteroaryl or substituted heteroaryl, except $R_{15}$ is not hydrogen;

$R_{18}$ is hydrogen, alkyl or substituted alkyl, alkenyl or substituted alkenyl, alkynyl or substituted alkynyl, cycloalkyl or substituted cycloalkyl, heterocycle or substituted heterocycle, heteroaryl, or substituted heteroaryl, aryl or substituted aryl; and m is 0, 1, 2 or 3;

provided that the following compounds are excluded:

(A) compounds having the formula (I), wherein $R_1$ is an optionally-substituted phenyl, pyridyl, pyridazinyl, pyrimidinyl, or pyrazinyl ring; $R_2$ is $R_{2a}$; $R_3$ is hydrogen; $R_4$ is methyl; m is 0; and X—$R_6$ is —C(=O)NH($C_{1-6}$alkyl), —C(=O)NH(cyclopropyl), or optionally-substituted oxadiazolyl;

(B) compounds having formula (Ix):

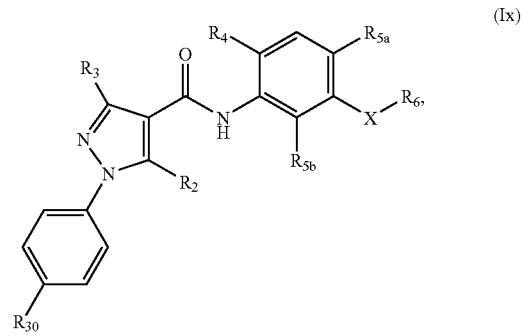

where (i) simultaneously, $R_{30}$ is trifluoromethyl, $R_2$ is methyl, $R_3$ is hydrogen, $R_4$ is bromo, X—$R_6$ is hydrogen, $R_{5b}$ is hydrogen, and $R_{5a}$ is methyl or

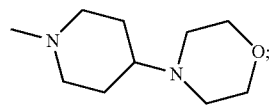

(ii) simultaneously, $R_{30}$ is hydrogen or methoxy, $R_2$ is hydrogen or methyl, $R_3$ is hydrogen, $R_4$ is hydrogen, X—$R_6$ is hydrogen, $R_{5b}$ is hydrogen, and $R_{5a}$ is trifluoromethyl;

(iii) simultaneously, $R_{30}$ is chloro, $R_2$ is hydrogen, $R_3$ is hydrogen, $R_4$ is hydrogen, X—$R_6$ is cyano, $R_{5b}$ is hydrogen, and $R_{5a}$ is $SR_{17}$ wherein $R_{17}$ is morpholinylalkyl;

(iv) simultaneously, $R_{30}$ is fluoro, $R_2$ is methyl, $R_3$ is hydrogen, $R_4$ is hydrogen, X—$R_6$ is cyano, $R_{5b}$ is hydrogen, and $R_{5a}$ is N-piperidinyl;

(v) simultaneously, $R_{30}$ is halogen, $R_2$ is hydrogen or methyl, $R_3$ is hydrogen, $R_4$ is hydrogen, X—$R_6$ is cyano, $R_{5b}$ is hydrogen, and $R_{5a}$ is heterocyclo or substituted heterocyclo;

(vi) simultaneously, $R_{30}$ is chloro, $R_2$ is trifluoromethyl, $R_3$ is hydrogen, $R_4$ is hydrogen, $X-R_6$ is $SO_2NH(cycloalkyl)$, and $R_{5a}$ and $R_{5b}$ are hydrogen;

(vii) simultaneously, $R_{30}$ is hydrogen, $R_2$ is trifluoromethyl, $R_3$ is hydrogen, $R_4$ is hydrogen, $X-R_6$ is hydrogen, $R_{5b}$ is hydrogen, and $R_{5a}$ is substituted alkyl;

(viii) simultaneously, $R_{30}$ is hydrogen, $R_2$ is trifluoromethyl, $R_3$ is hydrogen, $R_4$ is methyl, $X-R_6$ is hydrogen, $R_{5b}$ is $-C(=ONH(alkyl)$, and $R_{5a}$ is hydrogen; and (ix) simultaneously, $R_{30}$ is methoxy, $R_2$ is methyl, $R_3$ is hydrogen, $R_4$ is methyl, $X-R_6$ is a bicyclicheterocyclo(alkyl) or bicyclicheteroaryl(alkyl), and $R_{5a}$ and $R_{5b}$ are hydrogen; and (C) compounds having the formula (Iy),

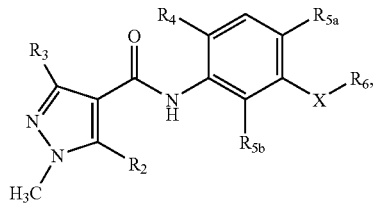

wherein (i) simultaneously, $R_2$ is hydrogen, $R_3$ is trifluoromethyl, $R_4$ is bromo, $X-R_6$ is hydrogen, $R_{5a}$ is trifluoromethyl, and $R_{5b}$ is bromo;

and wherein (ii) $R_2$ is methyl, $R_3$ is hydrogen, $R_4$ is hydrogen, $X-R_6$ is cyano, $R_{5a}$ is alkoxy, and $R_{5b}$ is hydrogen; and pharmaceutically acceptable salts and isomers thereof.

2. A compound according to claim 1, wherein $R_1$ is selected from:

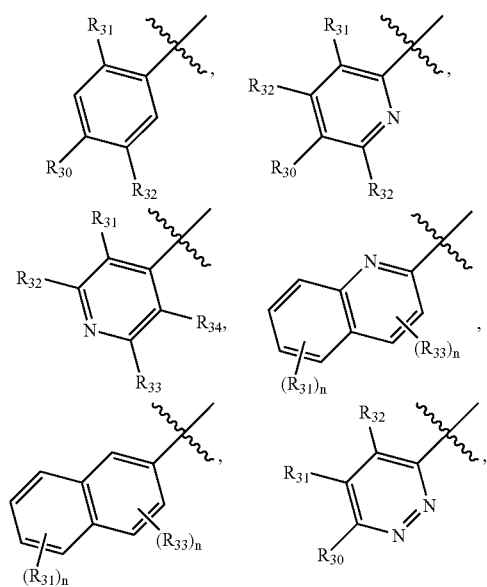

-continued

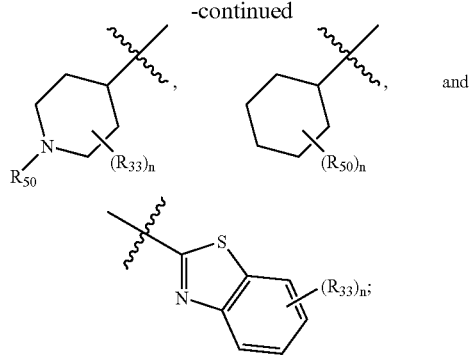

$R_{30}$, $R_{31}$, $R_{32}$, $R_{33}$ and $R_{34}$ are selected from hydrogen, halogen, cyano, trifluoromethyl, trifluoromethoxy, $C_{1-4}$alkyl, $O(C_{1-4}$alkyl), nitro, and/or $SO_2CH_3$; and $R_{50}$ is hydrogen, alkyl, or arylalkyl; and n is at each occurrence independently selected from 0-3; and/or pharmaceutically-acceptable salts, and isomers thereof.

3. A compound according to claim 1, wherein:

$R_1$ is optionally-substituted aryl or heteroaryl;

$R_2$ is hydrogen, lower alkyl, halogen, haloalkyl, trifluoromethyl, $NH_2$, $NH(alkyl)$, $NH(cycloalkyl)$, $N(alkyl)_2$, or $-CH_2-O-CH_3$, wherein each of said alkyl groups of $NH(alkyl)$, and/or $N(alkyl)_2$, are in turn optionally substituted with one to two of OH, $O(C_{1-4}$alkyl), imidazolyl, pyridyl, phenyl, tetrahydrofuryl, $NH_2$, $NH(alkyl)$, $N(alkyl)_2$, and N-morpholinyl;

$R_3$ is hydrogen or methyl;

$R_4$ is methyl or halogen;

X is $-C(=O)NH-$;

$R_6$ is lower alkyl, cyclopropyl, or optionally-substituted heteroaryl; and m is 0 or 1; and/or pharmaceutically-acceptable salts and isomers thereof.

4. A compound according to claim 1, having the formula,

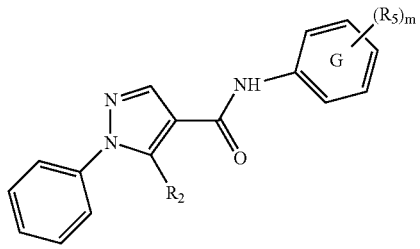

wherein G is phenyl, $R_5$ is halogen, hydroxyl, alkoxy, $C_{1-4}$alkyl, halo$C_{1-4}$alkyl, cyano, $SO_2(C_{1-4}$alkyl), nitro, heteroaryl, substituted heteroaryl, $-C(=O)NH(alkyl)$, or $-C(=O)NH(cycloalkyl)$; and/or pharmaceutically-acceptable salts and isomers thereof.

5. The compound of claim 1, wherein $R_3$ is hydrogen and $R_4$ is methyl.

6. The compound of claim 1, wherein G is phenyl and $R_6$ is a 5-membered heteroaryl which may be optionally substituted.

7. The compound of claim 6, wherein $R_2$ is lower alkyl, amino, or aminoalkyl, $R_3$ is hydrogen, $R_4$ is methyl or halogen, and m is 0.

8. The compound of claim 1, wherein $R_6$ is selected from the group consisting of:

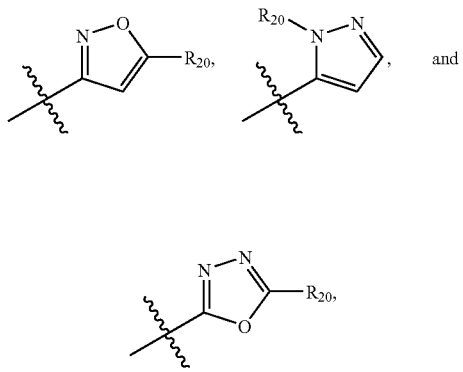

wherein $R_{20}$ is hydrogen, lower alkyl or phenyl.

9. A compound according to claim 1, wherein:
$R_1$ is optionally-substituted phenyl, pyridyl or pyradazinyl;
$R_{2a}$ is selected from the group consisting of amino, alkylamino, substituted alkylamino, cycloamino, substituted cycloamino, or $C_{1-6}$alkyl substituted with one to two of amino, alkylamino, substituted alkylamino, cycloamino, and/or substituted cycloamino;
$R_3$ is hydrogen;
$R_4$ is methyl;
X is —C(=O)NH—;
$R_6$ is lower alkyl, cyclopropyl, or an optionally-substituted pyrazolyl, imidazolyl, isoxazolyl, oxazolyl, or oxadiazolyl; and
m is 0 or 1; and/or pharmaceutically-acceptable salts and isomers thereof.

10. The compound of claim 9, wherein $R_6$ is selected from the group consisting of:

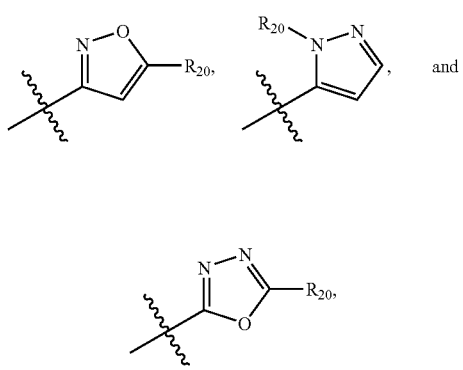

wherein $R_{20}$ is hydrogen, lower alkyl or phenyl.

11. A compound according to claim 9, wherein $R_1$ is selected from:

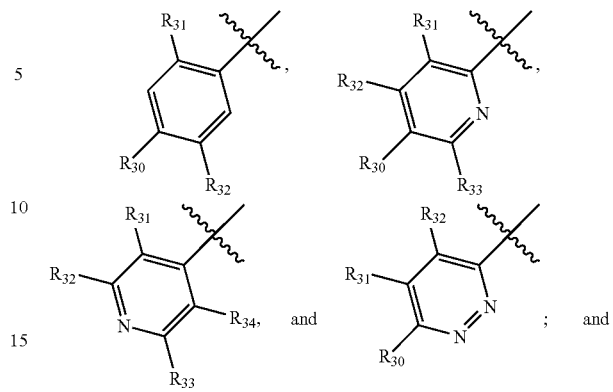

$R_{30}$, $R_{31}$, $R_{32}$, $R_{33}$ and $R_{34}$ are selected from hydrogen, halogen, cyano, trifluoromethyl, trifluoromethoxy, $C_{1-4}$alkyl, $O(C_{1-4}$alkyl), nitro, and $SO_2CH_3$.

12. A pharmaceutical composition comprising at least one compound according to claim 1 and a pharmaceutically-acceptable carrier or diluent.

13. A pharmaceutical composition comprising at least one compound according to claim 4 and a pharmaceutically-acceptable carrier or diluent.

14. A compound according to claim 1 wherein:
$R_1$ is phenyl optionally substituted by fluoro or pyridyl optionally substituted by $CF_3$;
$R_2$ is selected from the group consisting of H, —$CH_3$ and —$NH_2$;
$R_3$ is H or —$CH_3$;
$R_4$ is —$CH_3$ or Cl; and
$R_6$ is selected from the group consisting of —$CH_3$, cyclopropyl and isoxazole.

15. A compound according to claim 11 wherein:
$R_1$ is

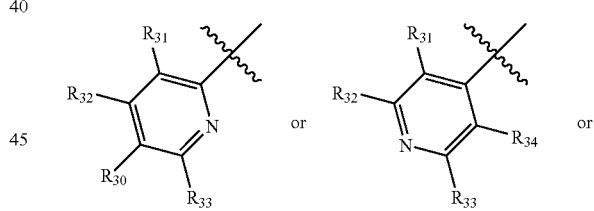

$R_2$ is —$CH_3$ or —$NH_2$;
$R_3$ is hydrogen or —$CH_3$;
$R_4$ is halo or —$CH_3$;
m is 0;
$R_6$ is cyclopropyl; and
$R_{30}$, $R_{31}$, $R_{32}$, $R_{33}$ and $R_{34}$ are each independently selected from the group consisting of hydrogen, —$CH_3$, —$OCH_2CH_3$, halogen, cyano and trifluoromethyl.

16. A compound according to claim 14 wherein $R_1$ is selected from the group consisting of:

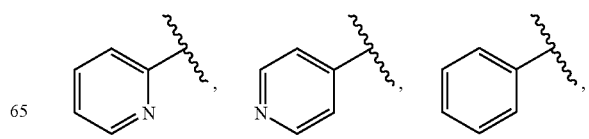

-continued
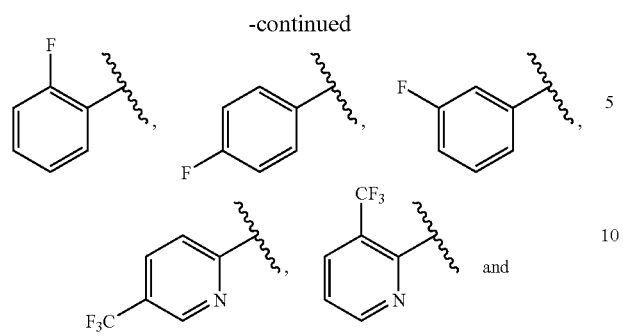
-continued
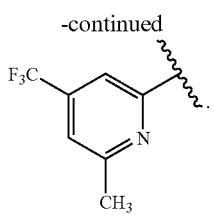
17. A compound according to claim 16 wherein $R_6$ is cyclopropyl.
* * * * *

UNITED STATES PATENT AND TRADEMARK OFFICE
CERTIFICATE OF CORRECTION

PATENT NO.       : 7,390,810 B2                                                Page 1 of 1
APPLICATION NO.  : 11/931309
DATED            : June 24, 2008
INVENTOR(S)      : Alaric J. Dyckman et al.

It is certified that error appears in the above-identified patent and that said Letters Patent is hereby corrected as shown below:

In the Claims:

Claim 2:

Column 101, lines 45 to 52, change

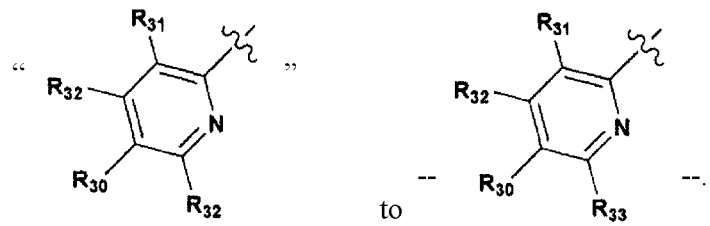

Claim 13:

Column 104, line 26, change "4" to -- 3 --.

Signed and Sealed this

Sixth Day of April, 2010

David J. Kappos
*Director of the United States Patent and Trademark Office*